(12) United States Patent
Chunduru et al.

(10) Patent No.: US 12,308,113 B1
(45) Date of Patent: May 20, 2025

(54) APPARATUS AND METHODS FOR SYNTHETIZING MEDICAL IMAGES

(71) Applicant: Anumana, Inc., Cambridge, MA (US)

(72) Inventors: Abhijith Chunduru, Bengaluru (IN); Uddeshya Upadhyay, Bengaluru (IN); Suthirth Vaidya, Bengaluru (IN); Sai Saketh Chennamsetty, Bengaluru (IN); Arjun Puranik, San Jose, CA (US)

(73) Assignee: Anumana, Inc., Cambridge, MA (US)

( * ) Notice: Subject to any disclaimer, the term of this patent is extended or adjusted under 35 U.S.C. 154(b) by 0 days.

(21) Appl. No.: 18/509,520

(22) Filed: Nov. 15, 2023

(51) Int. Cl.
*G06K 9/00* (2022.01)
*G06T 7/00* (2017.01)
*G16H 30/40* (2018.01)

(52) U.S. Cl.
CPC .......... *G16H 30/40* (2018.01); *G06T 7/0012* (2013.01); *G06T 2207/20081* (2013.01); *G06T 2207/20084* (2013.01); *G06T 2207/30048* (2013.01)

(58) Field of Classification Search
None
See application file for complete search history.

(56) References Cited

U.S. PATENT DOCUMENTS

| | | | |
|---|---|---|---|
| 7,940,972 B2 | 5/2011 | Wildes et al. | |
| 8,057,394 B2 | 11/2011 | Dala-Krishna et al. | |
| 8,428,690 B2 | 4/2013 | Li et al. | |
| 9,179,890 B2 | 11/2015 | Ionasec et al. | |
| 11,534,136 B2 | 12/2022 | Funka-Lea et al. | |
| 2019/0223819 A1* | 7/2019 | Mansi | G06T 15/205 |
| 2019/0357987 A1* | 11/2019 | Harks | A61B 34/20 |
| 2020/0289025 A1* | 9/2020 | Dichterman | G16H 40/63 |
| 2021/0217232 A1 | 7/2021 | Lupotti et al. | |

FOREIGN PATENT DOCUMENTS

WO    WO-2021209287 A1 *  10/2021  ............. G06T 11/00

OTHER PUBLICATIONS

Fanwei Kong et al; A deep-learning approach for direct whole-heart mesh reconstruction; Med Image Anal. Dec. 2021; 74: 102222. Published online Sep. 8, 2021.

Young-Ho Kim et al; Towards Automatic Manipulation of Intracardiac Echocardiography Catheter; IEEE Transaction on Medical Robotics and Bionics, Jul. 2020, Review-Only.

* cited by examiner

*Primary Examiner* — Wei Wen Yang
(74) *Attorney, Agent, or Firm* — Caldwell Intellectual Property Law

(57) ABSTRACT

An apparatus for synthetizing medical images, wherein the apparatus includes a process and a memory containing instructions configuring the processor to receive a heart model related to a patient's heart, identify a region of interest within the heart model, wherein identifying the region of interest includes locating at least a point of view on the heart model and determining a view angle corresponding to the at least a point of view, wherein the at least a point of view and the corresponding view angle define at least one field of view that include at least a portion of the heart model, and generate at least a medical image as a function of the region of interest using an image generator, wherein the at least a medical image captures an anatomical structure of the at least a portion of the heart model.

20 Claims, 9 Drawing Sheets

APPARATUS AND METHODS FOR SYNTHETIZING MEDICAL IMAGES

FIELD OF THE INVENTION

The present invention generally relates to the field of machine learning and medical imaging. In particular, the present invention is directed to apparatus and methods synthetizing medical images.

BACKGROUND

In the medical industry, medical images are typically used for real-time visualization during procedures; however, in some cases, medical images such as, without limitation, intracardiac echocardiography (ICE) images are not always saved post-procedure. In some cases, medical images may be useful for research and development purposes e.g., training machine learning models or testing new image processing techniques.

SUMMARY OF THE DISCLOSURE

In an aspect, an apparatus for synthetizing medical images is described. The apparatus includes at least a processor and a memory communicatively connected to the at least a processor, wherein the memory contains instructions configuring the at least a processor to receive a heart model related to a patient's heart, identify a region of interest within the heart model, wherein identifying the region of interest includes locating at least a point of view on the heart model and determining a view angle corresponding to the at least a view origin, wherein the at least a point of view and the corresponding view angle define at least one field of view that include at least a portion of the heart model. The at least a processor is further configured to generate at least a medical image as a function of the region of interest using an image generator, wherein the at least a medical image captures an anatomical structure of the at least a portion of the heart model.

In another aspect, a method for synthetizing medical images is illustrated. The method includes receiving, by at least a processor, a heart model related to a patient's heart, identifying, by the at least a processor, a region of interest within the heart model, wherein identifying the region of interest includes locating at least a point of view on the heart model and determining a view angle corresponding to the at least a view origin, wherein the at least a point of view and the corresponding view angle define at least one field of view that include at least a portion of the heart model. The method further includes generating, by the at least a processor, at least a medical image as a function of the region of interest using an image generator, wherein the at least a medical image captures an anatomical structure of the at least a portion of the heart model.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to apparatus and methods for synthesizing medical images. In an embodiment, a processor is configured to utilize a heart model derived from a statistical shape model to simulate and generate ICE images mimicking real-world clinical scenarios.

Aspect of the present disclosure may be used to train machine learning model that require medical images as input. Aspects of the present disclosure allow for greater versatility in research and development related to cardiac diagnostics. Exemplary embodiments illustrating aspects of the present disclosure are described below in the context of several specific examples.

Figure 1:
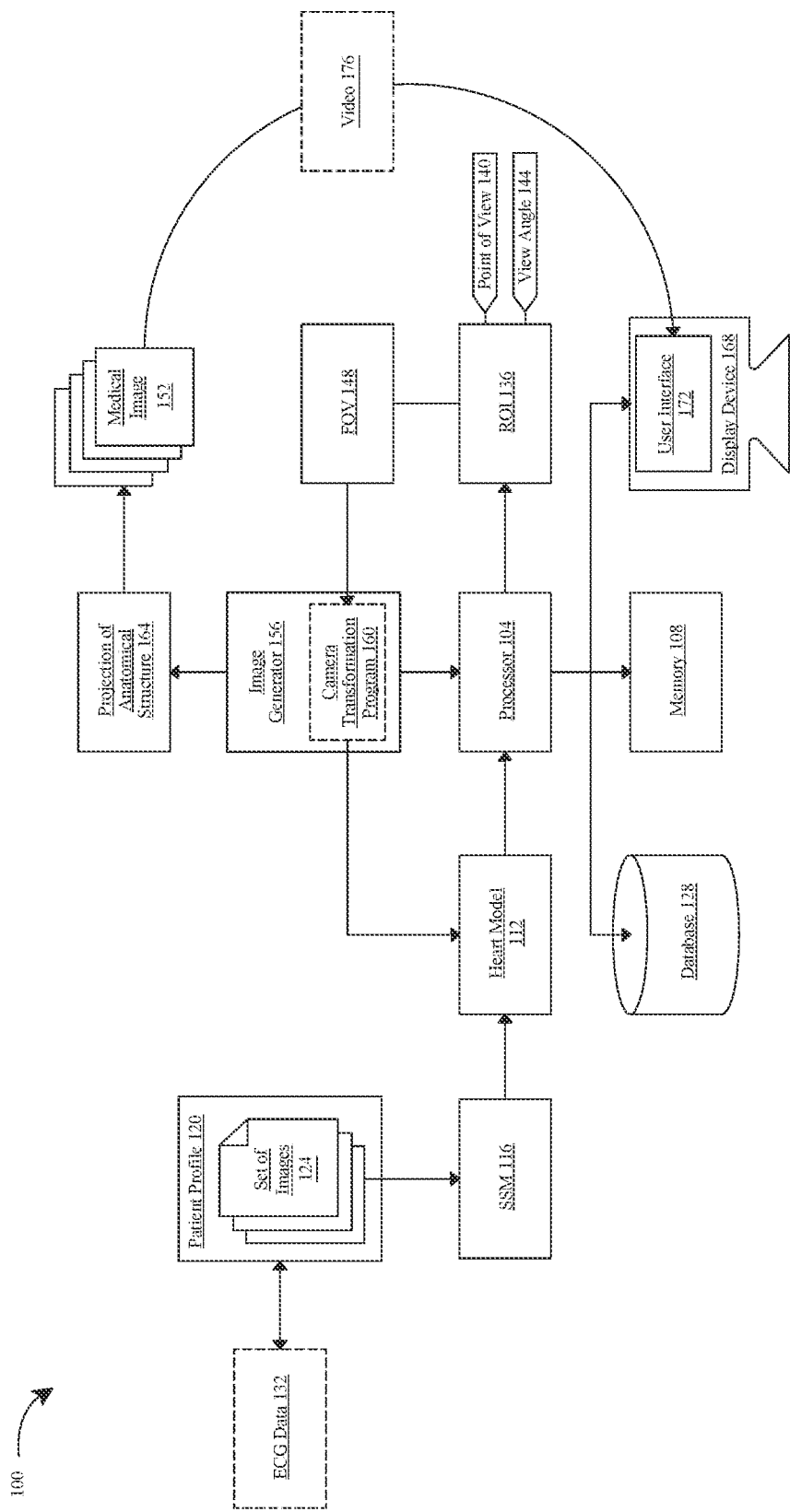
FIG. 1 is a block diagram of an exemplary embodiment of an apparatus for synthetizing medical images.

Referring now to FIG. 1, an exemplary embodiment of an apparatus 100 for generating 3D model of a cardiac anatomy via machine-learning is illustrated. System includes at least a processor 104. Processor 104 may include any computing device as described in this disclosure, including without limitation a microcontroller, microprocessor, digital signal processor (DSP) and/or system on a chip (SoC) as described in this disclosure. Computing device may include, be included in, and/or communicate with a mobile device such as a mobile telephone or smartphone. Processor 104 may include a single computing device operating independently, or may include two or more computing device operating in concert, in parallel, sequentially or the like; two or more computing devices may be included together in a single computing device or in two or more computing devices. Processor 104 may interface or communicate with one or more additional devices as described below in further detail via a network interface device. Network interface device may be utilized for connecting processor 104 to one or more of a variety of networks, and one or more devices. Examples of a network interface device include, but are not limited to, a network interface card (e.g., a mobile network interface card, a LAN card), a modem, and any combination thereof.

Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device. Processor 104 may include but is not limited to, for example, a computing device or cluster of computing devices in a first location and a second computing device or cluster of computing devices in a second location. Processor 104 may include one or more computing devices dedicated to data storage, security, distribution of traffic for load balancing, and the like. Processor 104 may distribute one or more computing tasks as described below across a plurality of computing devices of computing device, which may operate in parallel, in series, redundantly, or in any other manner used for distribution of tasks or memory between computing devices. Processor 104 may be implemented using a "shared nothing" architecture in which data is cached at the worker, in an embodiment, this may enable scalability of apparatus 100 and/or computing device.

With continued reference to FIG. 1, processor 104 may be designed and/or configured to perform any method, method step, or sequence of method steps in any embodiment described in this disclosure, in any order and with any degree of repetition. For instance, processor 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Processor 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, apparatus includes a memory 108 communicatively connected to at least a processor 104, wherein the memory 108 contains instructions configuring at least a processor 104 to perform any processing steps described herein. As used in this disclosure, "communicatively connected" means connected by way of a connection, attachment or linkage between two or more relata which allows for reception and/or transmittance of information therebetween. For example, and without limitation, this connection may be wired or wireless, direct or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio and microwave data and/or signals, combinations thereof, and the like, among others. A communicative connection may be achieved, for example and without limitation, through wired or wireless electronic, digital or analog, communication, either directly or by way of one or more intervening devices or components. Further, communicative connection may include electrically coupling or connecting at least an output of one device, component, or circuit to at least an input of another device, component, or circuit. For example, and without limitation, via a bus or other facility for intercommunication between elements of a computing device. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, processor 104 may perform determinations, classification, and/or analysis steps, methods, processes, or the like as described in this disclosure using machine-learning processes. A "machine-learning process," as used in this disclosure, is a process that automatedly uses a body of data known as "training data" and/or a "training set" (described further below in this disclosure) to generate an algorithm that will be performed by a processor 104/module to produce outputs given data provided as inputs; this is in contrast to a non-machine learning software program where the commands to be executed are determined in advance by a user and written in a programming language. Machine-learning process may utilize supervised, unsupervised, lazy-learning processes and/or neural networks, described further below.

With continued reference to FIG. 1, processor 104 is configured to receive a heart model 112 related to a patient's heart. As used in this disclosure, a "heart model" refers to a digital representation of patient's heart, capturing its anatomy, geometry, and potentially functional properties. In some cases, patient may include a human or any individual organism, on whom or on which the procedure, study, or otherwise experiment, such as without limitation, atrial fibrillation (AF) ablation, is being conducted. In a non-limiting example, processor 104 may receive heart model 112 of a human patient with AF who is undergoing a procedure, an individual undergoing cardiac screening, a participant in a clinical trial, patient with congenital heart disease, heart transplant candidate, patient receiving follow-up care after cardiac surgery, healthy volunteer, patient with heart failure, or the like. Additionally, or alternatively, patient may include an animal models (i.e., animal used to model AF such as a laboratory rat).

With continued reference to FIG. 1, in some cases, heart model 112 may be received from a statical shape model 116. as used in this disclosure, a "statistical shape model (SSM)" is a data structure representing, including, and/or utilizing a mathematical model that captures principal modes of variation in shape across a population of cardiac anatomies. SSM 116 captures a plurality of heart models associated with a plurality of patients. In some cases, SSM 116 may be used to capture the variability in anatomical structures among different patients; for instance, SSM 116 of the human heart may be constructed from a plurality of heart images of a plurality of individuals. In some cases, heart model 112 generated by SSM 116 may capture the "average" heart shape and main ways in which heart shapes may vary among the plurality of individuals. In a non-limiting example, SSM 116 described herein may be consistent with any SSM disclosed in U.S. patent application Ser. No. 18/376,688, filed on Oct. 4, 2023, and entitled "APPARATUS AND METHODS FOR GENERATING A THREE-DIMENSIONAL (3D) MODEL OF CARDIAC ANATOMY VIA MACHINE-LEARNING," which its entirety is incorporated herein by reference.

With continued reference to FIG. 1, in some cases, SSM 116 may be generated by processor 104 as a function of a set of labeled example shapes, each in a form of point-based representations or meshes. In some cases, example shapes may be represented in a 3D voxel occupancy representation (VOR). With continued reference to FIG. 1, in some cases, heart model 112 may include a 3D voxel occupancy representation (VOR) of the patient's heart. As used in this disclosure, a "3D voxel occupancy representation (VOR)" is a 3D digital representation of a spatial structure of the cardiac anatomy of a heart, wherein the representation is composed of a plurality of discrete volumetric elements known as voxels. A "voxel," for the purpose of this disclosure, is a 3D equivalent of a pixel in 2D imaging. While a pixel represents a point in a 2D image and may include properties such as color and/or brightness, a voxel may represent a volume in a 3D space and may include additional properties such density/occupancy as described below. In an embodiment, each voxel of plurality of voxels within 3D VOR may represent a specific portion of the heart.

With continued reference to FIG. 1, in some cases, voxel may be a smallest distinguishable box-shaped part (i.e., 1 px·x 1 px·x 1 px) of a three-dimensional image of a heart. In some cases, each voxel of plurality of voxels within 3D VOR may be represented as a cube or rectangular prism (although other shapes may be used in specialized applications). Each voxel may include a size that determines a resolution of the 3D image or model. In an embodiment, smaller voxels may provide higher resolution; however, it may require more computational resources (e.g., RAM) for processor 104 to process. In an embodiment, each voxel may include one or more embedded values (i.e., specific numerical or categorical data associated with each voxel). In some cases, embedded values may represent various attributes or characteristics of the corresponding portion a heart that voxel represents. In a non-limiting example, embedded values may include density values, intensity values, texture information, or any other quantitative measures that provide insights into the underlying cardiac tissue. In another non-limiting example, each voxel may include a presence indicator i.e., a data element that indicates a presence or absence (i.e., occupancy) of cardiac tissue within that portion as described in U.S. patent application Ser. No. 18/376,688. Such embedded values may be derived from the corresponding labels of the example shape.

With continued reference to FIG. 1, in some cases, processor 104 may be configured to align the set of labeled example shapes to a common reference frame using rigid, affine, or otherwise non-rigid registration methods to generate SSM 116. For example, and without limitation, the rigid registration might involve translations and rotations to superimpose the shapes; affine registration could incorporate scaling, shearing, and other linear transformations; while non-rigid methods might employ B-splines, thin-plate splines, or diffeomorphic transformations to flexibly map one shape onto another. In some cases, an averaged position of each corresponding point (or voxel) across all example shapes may be calculated using formula $$\bar{p}_i = \frac{1}{N}\sum_{j=1}^{N} p_{ji},$$

where $\bar{p}_i$ is the mean position of the ith point (or voxel), $p_{ij}$ is the position of the ith point in the jth example shape, and N is the total number of example shapes in the labeled set. In some cases, principle component analysis (PCA) may be applied to the aligned shapes to extract at least a primary mode of variation. As described herein, a "primary mode of variation" is a mode of variation that have the most significant variability, wherein the "mode of variation," for the purpose of this disclosure, is a specific pattern or direction of a shape change. In some cases, such significancy may be indicated by the first principal component in PCA. In some cases, a plurality of modes of variation may be extracted, wherein each mode (or principal component) may represent a specific way the shape of heart may be deformed from the mean shape, determined by one or more eigenvectors of the covariance matrix of the aligned shapes. In a non-limiting example, eigenvector with the highest eigenvalue may represent primary mode of variation which captures the largest amount of shape variability within example shapes, while subsequent modes (eigenvectors) capture decreasing amounts of variability.

With continued reference to FIG. 1, in some cases, once modes of variation are extracted, processor 104 may be configured to create a shape representation for any given heart shape within the studied class. In some cases, heart model 112 may be constructed using SSM 116, wherein the heart model 112 may integrate mean shape and plurality of modes of variation. In a non-limiting example, heart model 112 having a shape S may be mathematically represented as $$S = \bar{S} + \sum_{k=1}^{M} a_k \times \phi_k,$$

wherein S denotes the mean shape derived from the set of example shapes, M is the number of modes of variation considered, $a_k$ are the coefficients or weights for each mode, and $\phi_k$ are the modes of variation (eigenvectors corresponding to the kth principal component). In some cases, coefficients $a_k$ may dictate a degree to which each mode of variation is present in shape S. In some cases, coefficients $a_k$ may vary from positive to negative (or negative to positive) based on the deformation of the heart model 112 in directions described by each mode of variation. In some cases, heart model 112 may include mean shape as described herein. In some cases, heart model 112 may include a predictive heart shapes that may not have been explicitly seen in the set of example shapes or patient's heart observations. In some cases, heart model 112 may be in 3D VOR as described above.

With continued reference to FIG. 1, in some cases, processor 104 may be configured to construct heart model 112 based on a patient profile 120 using a computer vision module. As used in this disclosure, a "patient profile" is a comprehensive collection of information related to an individual patient. In some cases, patient profile may include a variety of different types of data that, when combined, provide a detailed picture of a patient's overall health. In an embodiment, patient profile may include demographic data of patient, for example, and without limitation, patient profile may include basic information about the patient such as name, age, gender, ethnicity, socioeconomic status, and/or the like. In another embodiment, each patient profile may also include a patient's medical history, for example, and without limitation, patient profile may include a detailed record of the patient's past health conditions, medical procedures, hospitalizations, and illnesses such as surgeries, treatments, medications, and/or the like. In another embodiment, each patient profile may include lifestyle Information of patient, for example, and without limitation, patient profile may include details about the patient's diet, exercise habits, smoking and alcohol consumption, and other behaviors that could impact health. In a further embodiment, patient profile may include patient's family history, for example, and without limitation, patient profile may include a record of hereditary diseases. As an ordinary person skilled in the art, upon reviewing the entirety of this disclosure, will be aware of various type of data within patient profiles apparatus 100 may receive and process in consistent with this disclosure.

With continued reference to FIG. 1, in one or more embodiments, patient profile 120 may include a set of images 124 of patient's heart and associated metadata. In some cases, set of images 124 may include a plurality of computed tomography (CT) scans of the patient's heart. Computed Tomography is a medical imaging technique that uses X-rays to capture cross-sectional images (slices) of the body. By taking a plurality of slices, a CT scan creates a detailed 3D representation of the internal structure. Other exemplary embodiments of set of images 124 may include, without limitation, X-ray images, magnetic resonance imaging (MRI) scans, ultrasound images, optical images, digital photographs, or any other form of visual data. A "computer vision module," for the purpose of this disclosure, is a computation component designed to perform one or more computer vision, image processing, and/or modeling tasks. In some cases, computer vision module may receive patient profile 120 and generate heart model 112 as a function of set of images 124 (and associated metadata). In one or more embodiment, computer vision module may include an image processing module. In some cases, set of images 124 may be pre-processed using an image processing module. As used in this disclosure, an "image processing module" is a component designed to process digital images such as set of images 124. For example, and without limitation, image processing module may be configured to compile plurality of images of a multi-layer scan to create an integrated image. In an embodiment, image processing module may include a plurality of software algorithms that can analyze, manipulate, or otherwise enhance an image, such as, without limitation, a plurality of image processing techniques as described below. In some cases, computer vision module may also include hardware components such as, without limitation, one or more graphics processing units (GPUs) that can accelerate the processing of large amount of images. In some cases, computer vision module may be implemented with one or more image processing libraries such as, without limitation, OpenCV, PIL/Pillow, ImageMagick, and the like. In a non-limiting example, one or more image processing tasks, such as noise reduction, contrast enhancement, intensity normalization, image segmentation and/or the like may be performed by computer vision module on plurality of CT scans to isolate heart and major vascular structures from surrounding tissues. In some cases, one or more machine learning models may be used to perform CT scans segmentations, for example, and without limitation, a U-net (i.e., a convolution neural network containing a contracting path as an encoder and an expansive path as a decoder, wherein the encoder and the decoder forms a U-shaped structure).

With continued reference to FIG. 1, in an embodiment, such segmentation of the heart may include a plurality of pixel values e.g., 0~255, each representing the presence of heart tissue at that location. In a non-limiting example, computer vision module may be configured to generate a mesh representation of patient's heart based on plurality of CT scan segmentations or other image segmentations, wherein the mesh representation may include a 3D VOR as described above, using Pix2Vox. Additionally, or alternatively, exemplary computer vision tasks may include, without limitation, object recognition, feature detection, edge/corner detection, and the like. Non-limiting examples of feature detection may include scale invariant feature transform (SIFT), Canny edge detection, Shi Tomasi corner detection, and the like. In some cases, generating mesh representation of patient's heart may include employing, by computer vision module, one or more transformations to orient one or more images relative a 3D coordinate system; exemplary transformations include without limitation homography transforms and affine transforms. Computer vision model may implement one or more 3D modeling algorithms, such as without limitation, marching cubes, contour detection and segmentation, active contour models, and/or the like to generate a coherent 3D representation based on the mesh representation of patient's heart e.g., heart model 112. In other cases, generic 3D modeling techniques may be applied by computer vision module to generate heart model 112. In some cases, generic 3D modeling techniques may include surface modeling, solid modeling, or parametric modeling, among others. As an ordinary person skilled in the art, upon reviewing the entirety of this disclosure, will be aware of various image processing, computer vision, and modeling tasks may be performed by processor 104 to generate heart model 112 of patient's heart from set of heart images.

With continued reference to FIG. 1, in some cases, processor 104 may be configured to perform shape extraction from segmented CT scans, for example, and without limitation, marching cubes algorithm or similar techniques may be employed to convert the voxel-based representation from CT segmentation into a mesh, wherein the mesh may represent the outer surface of the patient's heart. In some cases, the mesh may vary in resolutions, with more grid capturing finer details. In some cases, a consistent number of landmark points may be used to represent patient's heart surface. In a non-limiting example, one or more landmark points may be manually annotated by professional e.g., medical expert, ensuring that the landmark points correspond to specific anatomical locations of patient's heart. In other cases, they may be automatically derived using one or more computer vision algorithms as described herein. Landmark points may be uniformly spaced across the surface of extracted shape. In some cases, the size of the heart shape may be normalized so that the number of landmark points remain consistent between different heart shapes. In some cases, SSM 116 may include an implementation of generalized Procrustes analysis (GPA) to find a desired rigid transformation (translation, rotation) that aligns the set of example shapes. In a non-limiting example, processor 104 may be configured to minimize the sum of squared distance between corresponding landmark points across each heart shape. In some cases, size normalization may be reverted after alignment after such alignment. Constructing heart model 112 may include combining the mean shape computed by averaging the positions of corresponding landmarks points and one or more modes of variations. In a non-limiting example, heart model 112 may include a template model generated based a plurality of standard anatomical templates as described in U.S. patent application Ser. No. 18/376,688.

With continued reference to FIG. 1, in some cases, receiving heat model 112 may include extracting set of images 124 from patient profile (subsequent to patient identity verification and obtaining consent from subject). In some cases, patient profile may be obtained through hospital information system (HIS) or any other data acquisition platform to securely access patient's electronic medical record (EMR) or other relevant databases. set of images 124 may be directly or indirectly downloaded or exported. In some cases, each CT scan of set of images 124 may be in a usable and/or computer-readable format such as, without limitation, DICOM format, and necessary metadata such as, without limitation, patient information, study information, image modality, CT scanner information, slice thickness, pixel spacing, matrix size, and/or the like may be included. In some cases, metadata may also include acquisition parameters such as, without limitation, tube voltage (kV), tube current (mA), exposure time, total dose length product (DLP), CT dose index (CTDI), rotation time, number of acquisitions, contrast agent used (if any), contrast phase, and/or the like. In some cases, receiving heart model 112 may include recording the access and extraction of set of images 124 from patient profile 120; for instance, and without limitation, this process may be documented, by processor 104, in the patient's medical record, databases, or other appropriate logs.

With continued reference to FIG. 1, in some cases, heart model 112 may be directly imported from a dedicated database 128 or repository containing pre-constructed anatomical models. In some cases, database 128 may be based on historical patient scans, expert-constructed models, and/or the like. For instance, and without limitation, a heart model repository may consist of models derived from diverse population, capturing various cardiac pathologies, anomalies, or physiological states. Database 128 may be implemented, without limitation, as a relational database, a key-value retrieval database such as a NOSQL database, or any other format or structure for use as a database that a person skilled in the art would recognize as suitable upon review of the entirety of this disclosure. Database 128 may alternatively or additionally be implemented using a distributed data storage protocol and/or data structure, such as a distributed hash table or the like. Database 128 may include a plurality of data entries and/or records as described above. Data entries in database 128 may be flagged with or linked to one or more additional elements of information, which may be reflected in data entry cells and/or in linked tables such as tables related by one or more indices in database 128 or another relational database. Persons skilled in the art, upon reviewing the entirety of this disclosure, will be aware of various ways in which data entries in a database may store, retrieve, organize, and/or reflect data and/or records as used herein, as well as categories and/or populations of data consistently with this disclosure.

With continued reference to FIG. 1, it should be noted that SSM 116 may not be the only method for receiving heart model 112. For example, in some cases, heart model 112 may be directly imported from one or more external sources. In a non-limiting example, heart model 112 may be received from a dedicated computer software e.g., specialized software solutions available for medical imaging and 3D model generation. In some cases, heart model 112 may be exported such software which may provide model segmentation, rendering, and generation capabilities tailored for cardiac structures. In another non-limiting example, one or more third-party platforms (for patient data management diagnostic imaging, and other healthcare functionalities) that support DICOM standards may allow for extraction and sharing heart model 112 for synthetizing medical images as described in detail below. In a non-limiting example, heart model 112 may be received from several medical imaging and modeling services that are available on cloud. Such heart model 112 may be sourced from a cloud-based service (e.g., SaaS).

With continued reference to FIG. 1, in one or more embodiments, receiving the heart model may include transforming heart model 112 to a second heart model as a function of a plurality of mode changers within SSM 116, wherein each mode changer of the plurality of mode changers is associated with a model feature of heart model 112. As used in this disclosure, a "mode changer" is an algorithmic component derived from PCA configured to encapsulate a specific mode of variation as described above (representing a distinct way in which the shape of heart model 112 may deviate from the mean shape). A "model feature," for the purpose of this disclosure, is a distinct, recognizable and quantifiable attribute or characteristic of the heart model 112. For example, and without limitation, model feature may include an anatomical feature such as the size and curvature of the ventricles, the thickness of the heart wall, the positioning of heart valves or the like. In a non-limiting example, a mode changer may be associated with the size variation of the left ventricle identified within heart model 112. Such mode changer may be adjusted to modify the volume of the left ventricle, resulting in a second heart model that mimics potential biological variations or specific patient conditions that is different from original heart model 112. In some cases, multiple mode changers of SSM 116 may be adjusted simultaneously.

With continued reference to FIG. 1, additionally, or alternatively, processor 104 may receive a plurality of shape parameter sets. In some cases, heart model 112 may be described directly using plurality of shape parameters. In some cases, shape parameters may correspond to a plurality of modes of variations or mode changers as described above. As used in this disclosure, a "shape parameters" are numerical values or descriptors that quantitatively represent the geometric or morphological characteristics of patient's heart. In a non-limiting example, plurality of shape parameters may include information and/or metadata calculated, determined, and/or extracted from patient profile 120 and/or set of images 124, such as, dimensions, angles, curvatures, surface areas, texture, symmetry, and/or the like. In other embodiments, processor 104 may be configured to parameterize (model) features (e.g., edges, textures, contours, and the like) using CNN described in detail below. Such parameterization may involve processor 104 to derive one or more shape parameters including one or more morphological descriptors that quantitatively describe patient's heart based on extracted features. In some cases, transforming heart model 112 may include adjusting one or more shape parameters by adjusting associated mode changers.

With continued reference to FIG. 1, in some cases, patient profile 120 may further include electrocardiogram (ECG) data 132, wherein the "ECG data," for the purpose of this disclosure, refers to data related to an electrocardiogram of the patient that corresponds to the patient profile. A "electrocardiogram," as described herein, is a medical test that records the electrical activity of subject's heart over a period of time. In an embodiment, ECG data 132 may include one or more recordings captured by a plurality of electrodes placed on patient's skin. In one or more embodiments, ECG data 132 may include information regarding a P wave, T wave, QRS complex, PR interval, ST segment, and/or the like. In some cases, ECG data 132 may be used to identify specific cardiac events or phases of a cardiac cycle e.g., isovolumic relaxation, ventricular filling, isovolumic contraction, and rapid ventricular ejection. In a non-limiting example, patient profile 120 and ECG data 132 described herein may be consistent with any patient profile and ECG data disclosed in U.S. patent application Ser. No. 18/229,854, filed on Aug. 3, 2023, entitled "APPARATUS AND METHOD FOR DETERMINING A PATIENT SURVIVAL PROFILE USING ARTIFICIAL INTELLIGENCE-ENABLED ELECTROCARDIOGRAM (ECG)," the entirety of which is incorporated herein by reference.

With continued reference to FIG. 1, processor 104 is configured to identify a region of interest (ROI) 136 within heart model 112. As described in this disclosure, a "region of interest" is a specific and pre-defined spatial subset of an image or a 3D model. In some cases, ROI 136 include a volume that has been designated for closer analysis or further processing as described in detail below due to its potential significance or relevance in synthesizing medical images. In some cases, identifying ROI 136 within heart model 112 may include isolating ROI 136 with surrounding structure of heart model 112 that may be less relevant. In some cases, ROI 136 may be manually selected by a user. In some cases, one or more graphical tools and/or imaging software may be used to outline a particular area on heart model 112 or an image captured from heart model 112. In other cases, processor 104 may be configured to automatically detect and define ROI 136. In an embodiment, a computer vision module configured to perform one or more computer vision tasks such as, without limitation, thresholding, edge detection, or machine learning process may be used to recognize ROI 136 with specific features or anomalies.

With continued reference to FIG. 1, in some cases, ROI 136 may also include temporal ROI. In an embodiment, ROI 136 may not be spatial but also temporal. In some cases, a specific timeframe within a sequence may be designated as a ROI. In a non-limiting example, temporal ROI may focus on a specific time segment or interval within a dynamic dataset e.g., heart model 112 with animation that simulating a cardiac cycle. In some cases, temporal ROI may change over time. For example, and without limitation, temporal ROI may include a time-series images capturing patient's heart activity, or a sequence showcasing blood flow within the cardiac structure. In a non-limiting example, ROI 136 may include a temporal ROI set to capture a specific phase of cardiac cycle such as systole or diastole. In other cases, ROI 136 may include a hierarchical ROI. In a non-limiting example, processor may identify one or more smaller sub-ROIs within a larger ROI, each with its significance or weight.

With continued reference to FIG. 1, identifying ROI 136 includes locating at least a point of view 140 on heart model 112 and determining a view angle 144 corresponding to the at least a point of view 140. As used in this disclosure, a "point of view" is a specific spatial location or origin form which an image or scene is observed or captured. In a non-limiting example, point of view 140 may be configured to mimic the location of a camera e.g., an intracardiac echocardiography (ICE) probe within or near patient's heart (without a magnetic field which is required in case of using a real ICE probe). Conventional Biosense/carto ICE catheter may use a specific magnetic location system-which requires specific equipment that creates magnetic field around the patient to generate a triangular location i.e., ROI 136. When patient moves, the magnetic coordinates remain the same but relative location in intracardiac chambers may change, yielding undesired results. In some cases, at least a point of view 140 may be imagined as the location of the ICE probe or other probe's tip. In some cases, at least a point of view 140 may determine from where within heart model 112 or its vicinity the "pseudo" ultrasound waves are emitted and received. Given that ICE is a type of endoluminal ultrasound, in some cases, at least a point of view 140 may be intracardiac which may be located inside heart chambers. Exemplary point of view may include, without limitation, ventricular point of view, atrial point of view, near-valvular point of view, and/or the like. In a non-limiting example, ROI 136 may be identified and at least a point of view 140 may be located on the left ventricle's wall, targeting its thickness and motion to assess potential cardiomyopathy.

With continued reference to FIG. 1, a "view angle," for the purpose of this disclosure, is an angular orientation or direction from at least a point of view 140. In some cases, view angle 144 may determine the segment of the scene or image that is visible or captured. In some cases, at least a point of view 140 and corresponding view angle 144 defines at least one field of view (FOV) 148 that include at least a portion of heart model 112. In a non-limiting example, view angle 144 may reflect the orientation of an imaging plane relative to the structure of interest within identified ROI 136. In some cases, view angle 144 corresponding to at least a view point 140 may define the tilt of the imaging plane, determining which structures come into FOV 148. In some cases, FOV 148 may indicate an area of a scene that may be captured by a camera within defined bounds (e.g., spatial boundary of ROI 136) of heart model 112. Exemplary view angle 144 may include apical view (visualize patient's heart from its apex), parasternal view (oriented laterally from the mid-sternal line), subcostal view (with angle inferiorly positioned). In some cases, view angle 144 may be corresponding to the angle of the sector of a resultant medical image such as an ICE image as described in detail below (resembles a sector or-pie slice shape), wherein the ICE probe tip may act as the sector's apex (i.e., point of view 140) that delineates the ultrasound wave's spread and hence, the captured anatomy's width. In a non-limiting example, a narrower view angle may be chosen to focus on a specific region of patient's heart e.g., a valve. Conversely, a broader view angle may capture more extensive heart region, offering a comprehensive overview of heart model 112.

With continued reference to FIG. 1, in an embodiment, one or more machine learning models may be used to automatically identify a desired ROI 136 that captures most clinically relevant portion of heart model 112. In such an embodiment, desired ROI 136 may include key anatomical structures or pathological indicators. processor 104 may use a machine learning module to implement one or more algorithms as described herein or generate one or more machine learning models, such as a ROI identification model to identify ROI 136 within heart model 112. However, the machine learning module is exemplary and may not be necessary to generate one or more machine learning models and perform any machine learning described herein. In one or more embodiments, one or more machine-learning models may be generated using training data. Training data may include inputs and corresponding predetermined outputs so that a machine-learning model may use correlations between the provided exemplary inputs and outputs to develop an algorithm and/or relationship that then allows machine-learning model to determine its own outputs for inputs. Training data may contain correlations that a machine-learning process may use to model relationships between two or more categories of data elements. Exemplary inputs and outputs may come from a database, such as any database described in this disclosure, or be provided by a user. In other embodiments, a machine-learning module may obtain a training set by querying a communicatively connected database that includes past inputs and outputs. Training data may include inputs from various types of databases, resources, and/or user inputs and outputs correlated to each of those inputs so that a machine-learning model may determine an output. Correlations may indicate causative and/or predictive links between data, which may be modeled as relationships, such as mathematical relationships, by machine-learning models, as described in further detail below. In one or more embodiments, training data may be formatted and/or organized by categories of data elements by, for example, associating data elements with one or more descriptors corresponding to categories of data elements. As a non-limiting example, training data may include data entered in standardized forms by persons or processes, such that entry of a given data element in a given field in a form may be mapped to one or more descriptors of categories. Elements in training data may be linked to descriptors of categories by tags, tokens, or other data elements. In a further embodiment, training data may include previous outputs such that one or more machine learning models iteratively produces outputs.

With continued reference to FIG. 1, in some cases, ROI identification model may be trained using training data containing a plurality of annotated heart models as input correlated to a plurality of desired ROIs as output. In some embodiments, training data for ROI identification model may also include a plurality of heart models and patient profiles including associated metadata (e.g., patient information, study information, acquisition parameters, and/or the like as described above) as input correlated to a plurality of point of views and corresponding view angles as output. In such embodiment, processor 104 may recognize and highlight at least a point of view and a corresponding view angle for each heart model based on associated metadata, wherein the at least a point of view and the corresponding view angle may together define a field of view that related to a desired ROI. Processor 104 may then be configured to identify ROI 136 using the trained ROI identification model. Automatically identification of ROI 136 as described herein may overcome the afore mentioned limitations of magnetic location system, wherein the location and orientation of the ICE probe may be looked up reversely through ROI identification model.

With continued reference to FIG. 1, processor 104 is configured to generate at least a medical image 152 as a function of ROI 136 using an image generator 156. As used in this disclosure, a "medical image" is a visualization of the interior of a body to diagnose, monitor, or provide information about the internal structures, organs, or systems of the patient. In some cases, medical image 152 may include, without limitation, X-ray image, echocardiogram, magnetic resonance imaging (MRI) scan, CT scan, ultrasound image, optical image, digital photograph, and/or the like. In a non-limiting example, medical image 152 may include an intracardiac echocardiography (ICE) image. As used in this disclosure, an "ICE image" is an ultrasound image obtained from within the heart's chambers or blood vessels. In some cases, at least an ICE image may be captured using a specialized catheter equipped with an ultrasound transducer that is inserted into the body and guided to the heart of subject. In an embodiment, at least a medical image 152 may provide a detailed and real-time visualizations of cardiac anatomy i.e., structural composition of patient's heart and its associated blood vessels. In a non-limiting example, at least a medical image 152 may include at least an ICE image captures an anatomical structure of the at least a portion of heart model 112. In some cases, anatomical structure may include, without limitation, chambers (e.g., four chambers including left and right atria and left and right ventricles), valves (i.e., the structures that regulate blood flow between chambers and vessels, including mitral, tricuspid, aortic, and pulmonary valves), vessels (e.g., aorta, pulmonary arteries and veins, and coronary arteries), conduction system (i.e., a network of specialized cells that control the heart's electrical activity and rhythm), muscular and connective tissues (e.g., heart's muscular walls, septa, any other connective tissues that provide structural integrity and enable contraction), LAA and other appendages, pathological features (e.g., any abnormalities, defects, and/or the like), among others.

With continued reference to FIG. 1, in a non-limiting example, at least a medical image 152 may include a particular view of patient's heart chambers, valves, vessel, and/or the like. In some cases, processor 104 may be configured to generate a plurality of medical images, or at least a medical image 152 containing a plurality of views e.g., different angles and perspectives of heart model 112. In some cases, plurality of medical images may be arranged in a temporal sequence. In a non-limiting example, plurality of medical images may include a series of ICE images captured over time, allowing for an observation of dynamic cardiac functions such as beating, blood flow, and/or the like as described above. In some cases, at least a medical image 152 may include a corresponding timestamp, wherein the timestamp may include an indicator showing a date and time of when the corresponding ICE image was generated. In a further non-limiting example, at least an ICE image may include a synthetic ICE frame as described in detail below with reference to FIG. 3

With continued reference to FIG. 1, as used in this disclosure, an "image generator" is a system, apparatus, or software module designed to produce or synthesize visual representations (images) based on certain input data. In an embodiment, image generator 156 may be configured to generate at least a medical image 152 based on input data such as, without limitation, heart model 112, ROI 136, at least a point of view 140 and corresponding view angle 144, among others. In some cases, generation performed by image generator 156 may be rooted in real-world data, simulated data, or a combination of both. In some cases, image generator 156 include a software component that processes raw data from one or more imaging device e.g., MRI, CT, or ultrasound machines, and reconstruct it into interpretable visual displays.

With continued reference to FIG. 1, in some cases, image generator 156 may include implementations of one or more camera transformation programs 160. As used in this disclosure, a "camera transformation program" is a software or algorithm that manipulate location, perspective, and orientation of a virtual camera in relation to an object or scene. In an embodiment, camera transformation program 160 may be executed to effectively transform or alter how heart model 112 within ROI 136 is visualized, simulating the effects of physically moving or adjusting a real-world camera e.g., an ICE probe or other probe. In some cases, camera transformation program 160 may involve moving at least a virtual camera's potion in 3D space. In some cases, virtual camera may be placed at the at least a point of view 140. In some cases, virtual camera may be in the same object space with heart model 112. In a non-limiting example, camera transformation program 160 may include translation configured to shift camera left, right, up, down, forward, or backward. In some cases, camera transformation program 160 may include one or more instructions on configuring virtual camera's orientation based on a horizontal or vertical axes, for example, and without limitation, virtual camera may be configured to pitch (tilt up or down), yaw (turn left or right), or roll (tilt sideways). In some cases, camera transformation program 160 may adjust virtual camera's perspective to "zoom" in or out on heart model 112. In a non-limiting example, generating at least a medical image 152 may include generating at least an ICE image by executing camera transformation program 160 to simulate at least a perspective of an ICE probe or other probe using the image generator 156.

With continued reference to FIG. 1, in one or more embodiment executing camera transformation program 160 may include generating a projection of the anatomical structure 164 by rendering ROI 136 as a function of a set of imaging parameters using virtual camera positioned at the at least a point of view 140 with the corresponding view angle 144. As used in this disclosure, an "anatomical structure projection" is a depiction of a 3D anatomical structure such as a part of heart model 112 onto a 2D plane or surface. In some cases, such projection of anatomical structure may capture spatial and/or morphological features of one or more anatomical structure as described herein as it would appear from at least a view point 140 or under certain imaging parameters. As used in this disclosure, a "set of imaging parameters" refers to a collection of specific variables and configurations (of virtual camera) that determined how medical image 152 are generated, processed, and visualized. In some cases, set of imaging parameters may replicate the intricacies of real-world ICE imaging. In some cases, users e.g., clinicians or medical professionals may manually set or adjust set of imaging parameters through user interface as described below. In other cases, imaging parameters may be auto-detected based on an initial generation of medical image 152 and/or preliminary data. For example, and without limitation, image parameters may include a pre-defined set of parameters configured for viewing particular heart regions or structures of the mean shape. One or more machine learning models as described herein may be implemented to adjust set of image parameters iteratively based on the quality or clarity of the initial scan until a desired medical image are achieved.

With continued reference to FIG. 1, in a non-limiting example, camera transformation program 160 may be configured to simulate projection as if an ICE probe or other probe is inserted from the apex of the patent's heart and angled towards the mitral valve, giving a detailed view of the valve's leaflets and adjoining heart structures. In some cases, camera transformation program 160 may be configured to determine how 3D objects e.g., heart model 112 are projected onto 2D visual plane. Exemplary image projections may include, without limitation, orthographic (parallel) projection, perspective (converging lines) projection, and the like. In a non-limiting example, for a close-up detailed view of ROI 136 without depth distortions, an orthographic projection may be preferred, while for a more holistic view of how structures related to one another in 3D space, a perspective projection may be more apt.

With continued reference to FIG. 1, in one or more embodiments, processor 104 may implement one or more aspects of "generative artificial intelligence (AI)," a type of AI that uses machine learning algorithms to create, establish, or otherwise generate data such as, without limitation, medical image 152 as described herein that is similar to one or more provided training examples. In an embodiment, machine learning module described herein may generate one or more generative machine learning models that are trained on one or more set of example medical images previously generated. One or more generative machine learning models may be configured to generate new examples that are similar to the training data of the one or more generative machine learning models but are not exact replicas; for instance, and without limitation, data quality or attributes of the generated examples may bear a resemblance to the training data provided to one or more generative machine learning models, wherein the resemblance may pertain to underlying patterns, features, or structures found within the provided training data.

With continued reference to FIG. 1, in some cases, image generator 156 may include a generative machine learning model having one or more generative models. As described herein, "generative models" refers to statistical models of the joint probability distribution $P(X, Y)$ on a given observable variable x, representing features or data that can be directly measured or observed (e.g., heart model 112, set of images 124 and associated metadata, among others) and target variable y, representing the outcomes or labels that one or more generative models aims to predict or generate (e.g., medical image 152). In some cases, generative models may rely on Bayes theorem to find joint probability; for instance, and without limitation, Naïve Bayes classifiers may be employed by computing device to categorize input data such as, without limitation, heart model 112 derived from CT scans into different views.

With continued reference to FIG. 1, in a non-limiting example, one or more generative machine learning models may include one or more Naïve Bayes classifiers generated, by processor 104, using a Naïve bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)=P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Processor 104 may then calculate a likelihood table by calculating probabilities of different data entries and classification labels. Processor 104 may utilize a naïve Bayes equation to calculate a posterior probability for each class. A class containing the highest posterior probability is the outcome of prediction.

With continued reference to FIG. 1, although Naïve Bayes classifier may be primarily known as a probabilistic classification algorithm; however, it may also be considered a generative model described herein due to its capability of modeling the joint probability distribution $P(X, Y)$ over observable variables X and target variable Y. In an embodiment, Naïve Bayes classifier may be configured to make an assumption that the features X are conditionally independent given class label Y, allowing generative model to estimate the joint distribution as $P(X, Y) = P(Y)\Pi_i P(X_i|Y)$, wherein $P(Y)$ may be the prior probability of the class, and $P(X_i|Y)$ is the conditional probability of each feature given the class. One or more generative machine learning models containing Naïve Bayes classifiers may be trained on labeled training data, estimating conditional probabilities $P(X_i|Y)$ and prior probabilities $P(Y)$ for each class; for instance, and without limitation, using techniques such as Maximum Likelihood Estimation (MLE). One or more generative machine learning models containing Naïve Bayes classifiers may select a class label y according to prior distribution $P(Y)$, and for each feature $X_i$, sample at least a value according to conditional distribution $P(X_i|y)$. Sampled feature values may then be combined to form one or more new data instance with selected class label y. In a non-limiting example, one or more generative machine learning models may include one or more Naïve Bayes classifiers to generate new medical images such as ICE images as a function of input data such as, without limitation, at least a point of view 140 and corresponding view angle 144, wherein the models may be trained using training data containing a plurality of heart models and ROIs as described herein as input correlated to a plurality of ICE images.

With continued reference to FIG. 1, in some cases, one or more generative machine learning models may include generative adversarial network (GAN). As used in this disclosure, a "generative adversarial network" is a type of artificial neural network with at least two sub models (e.g., neural networks), a generator, and a discriminator, that compete against each other in a process that ultimately results in the generator learning to generate new data samples, wherein the "generator" is a component of the GAN that learns to create hypothetical data by incorporating feedbacks from the "discriminator" configured to distinguish real data from the hypothetical data. In some cases, generator may learn to make discriminator classify its output as real. In an embodiment, discriminator may include a supervised machine learning model while generator may include an unsupervised machine learning model as described in further detail with reference to FIGS. 5-7.

With continued reference to FIG. 1, in an embodiment, discriminator may include one or more discriminative models, i.e., models of conditional probability $P(Y|X=x)$ of target variable Y, given observed variable X. In an embodiment, discriminative models may learn boundaries between classes or labels in given training data. In a non-limiting example, discriminator may include one or more classifiers as described in further detail below with reference to FIG. 5 to distinguish between different categories e.g., real vs. fake, or states e.g., TRUE vs. FALSE within the context of generated data such as, without limitations, generated medical image 152, and/or the like. In some cases, processor 104 may implement one or more classification algorithms such as, without limitation, Support Vector Machines (SVM), Logistic Regression, Decision Trees, and/or the like to define decision boundaries.

With continued reference to FIG. 1, in a non-limiting example, generator of GAN may be responsible for creating synthetic data that resembles real medical images. In some cases, GAN may be configured to receive heart model 112 and/or set of images 124 as input and generates corresponding examples of medical images containing information describing heart anatomy in different ICE views. In some cases, processor 104 may be configured to train GAN using a plurality of anatomical structure projections 164 as described above and synthesizing at least a medical image 152 using the trained GAN at the at least a point of view 140 with corresponding view angle 144. In some cases, during synthesizing at least a medical image 152, discriminator of GAN may evaluate the authenticity of the generated content by comparing it to true medical images, for example, discriminator may distinguish between genuine and generated content and providing feedback to generator to improve the model performance. Additionally, or alternatively, GAN may include a conditional GAN as an extension of the basic GAN as described herein that allows for generation of medical images using heart model 112 and/or set of images 124 based on certain conditions or labels. In standard GAN, generator may produce samples from random noise, while in a conditional GAN, generator may produce samples based on random noise and a given condition or label.

With continued reference to FIG. 1, additionally, or alternatively, one or more generative models may also include a variational autoencoder (VAE). As used in this disclosure, a "variational autoencoder" is an autoencoder (i.e., an artificial neural network architecture) whose encoding distribution is regularized during the model training process in order to ensure that its latent space includes desired properties allowing new data sample generation. In an embodiment, VAE may include a prior and noise distribution respectively, trained using expectation-maximization meta-algorithms such as, without limitation, probabilistic PCA, sparse coding, among others. In a non-limiting example, VEA may use a neural network as an amortized approach to jointly optimize across input data and output a plurality of parameters for corresponding variational distribution as it maps from a known input space to a low-dimensional latent space. Additionally, or alternatively, VAE may include a second neural network, for example, and without limitation, a decoder, wherein the "decoder" is configured to map from the latent space to the input space.

With continued reference to FIG. 1, in some cases, processor 104 may be configured to continuously monitor image generator 156. In an embodiment, processor 104 may configure discriminator to provide ongoing feedback and further corrections as needed to subsequent input data. An iterative feedback loop may be created as processor 104 continuously receive real-time data, identify errors (e.g., distance between generated medical image 152 and real medical images) as a function of real-time data, delivering corrections based on the identified errors, and monitoring subsequent model outputs and/or user feedbacks on the delivered corrections. In an embodiment, processor 104 may be configured to retrain one or more generative machine learning models within image generator 156 based on user modified/annotated medical images or update training data of one or more generative machine learning models within image generator 156 by integrating validated medical images (i.e., subsequent model output) into original training data. In such embodiment, iterative feedback loop may allow image generator 156 to adapt to the user's needs and performance requirements, enabling one or more generative machine learning models described herein to learn and update based on user responses and generated feedbacks.

With continued reference to FIG. 1, other exemplary embodiments of generative machine learning models may include, without limitation, long short-term memory networks (LSTMs), (generative pre-trained) transformer (GPT) models, mixture density networks (MDN), and/or the like. As an ordinary person skilled in the art, upon reviewing the entirety of this disclosure, will be aware of various generative machine learning models that may be used to generate medical image 152 as described herein. In a further non-limiting embodiment, image generator 156 may be further configured to generate a multi-model neural network that combines various neural network architectures described herein. In a non-limiting example, multi-model neural network may combine LSTM for time-series analysis with GPT models for natural language processing. Such fusion may be applied by computing device to generate medical image 152. In some cases, multi-model neural network may also include a hierarchical multi-model neural network, wherein the hierarchical multi-model neural network may involve a plurality of layers of integration; for instance, and without limitation, different models may be combined at various stages of the network. Convolutional neural network (CNN) may be used for image feature extraction, followed by LSTMs for sequential pattern recognition, and a MDN at the end for probabilistic modeling. Other exemplary embodiments of multi-model neural network may include, without limitation, ensemble-based multi-model neural network, cross-modal fusion, adaptive multi-model network, among others. As an ordinary person skilled in the art, upon reviewing the entirety of this disclosure, will be aware of various generative machine learning models that may be used to synthetize medical images as described herein. As an ordinary person skilled in the art, upon reviewing the entirety of this disclosure, will be aware of various multi-model neural network and combination thereof that may be implemented by apparatus 100 in consistent with this disclosure.

With continued reference to FIG. 1, apparatus 100 may further include a display device 168. As used in this disclosure, a "display device" is an electronic device that visually presents information to a user. In an embodiment, display device may include an output interface that translates data such as, without limitation, generated medical image 152 from processor 104 or other computing devices into a visual form that can be easily understood by user. In some cases, generated medical image 152 and/or other data described herein such as, without limitation, heart model 112, patient profile 120, and/or the like may also be displayed through display device 168 using a user interface 172. User interface 172 may include a graphical user interface (GUI), wherein the GUI may include a window in which generated medical image 152 and/or other data described herein may be displayed. In an embodiment, user interface 172 may include one or more graphical locator and/or cursor facilities allowing user to interact with generated medical image 152 and/or any other data, or even process described herein, for instance, and without limitation, by using a touchscreen, touchpad, mouse, keyboard, and/or other manual data entry device, user may enter user input containing selecting specific regions, adding comments, adjusting parameter, and/or the like. In a non-limiting example, user interface 172 may include one or more menus and/or panels permitting selection of measurements, models, visualization of data/model to be displayed and/or used, elements of data, functions, or other aspects of data/model to be edited, added, and/or manipulated, options for importation of and/or linking to application programmer interfaces (APIs), exterior services, data source, machine-learning models, and/or algorithms, or the like. Persons skilled in the art, upon reviewing the entirety of this disclosure, will be aware of various ways in which a visual interface and/or elements thereof may be implemented and/or used as described in this disclosure.

With continued reference to FIG. 1, in some cases, processor 104 may be further configured to compile a plurality of medical images into a video 176 as a function of ECG data 132, wherein the video is synchronized with a cardiac cycle indicated by ECG data 132. As used in this disclosure, a "video" is a sequential arrangement of plurality of images played over time. In a non-limiting embodiment, video 176 may include an ICE video, wherein the ICE video may capture dynamic changes and movements within heart model 112 or related structures over a certain duration by playing a plurality of ICE images arranged based on ECG data 132. In some cases, processor 104 may be configured to identify distinct phases or cardiac cycle based on ECG data 132 including, but is not limited to P-wave, QRS complex, T-wave, and/or the like as described above. Plurality of ICE images may be segmented based on each ICE image's timestamp or acquisition sequence, associating each ICE image with a specific phase or time point within the cardiac cycle. Processor 104 may then synchronize the segmented ICE images with the corresponding phases of the cardiac cycle derived from ECG data 132, ensuring temporal alignment between echocardiographic visualizations and the electrophysiological events. In a non-limiting example, processor 104 may be configured to sequentially assemble plurality of medical images in accordance with the chronological progression of the cardiac cycle, resulting in a continuous video 176 that accurately reflects patient's heart's dynamic movements and changes in response to treatments. In some cases, one or more interpolation or frame blending techniques may be applied by processor 104 to ensure smooth transitions between consecutive medical images and eliminate visual discontinuities in the synthesized video 176. In a non-limiting example, an video such as an ICE video 176 synchronized with ECG data 132 may show valve's opening and closing in tandem with specific points on the ECG waveform e.g., P wave or T wave when observing the mitral valve's movement during a cardiac cycle.

With continued reference to FIG. 1, in some cases, plurality of generated medical images may be used as training data to train other machine learning models that requires consistent medical image input. In some cases, processor 104 may generate medical images training data by correlating generated medical images with sourced heart model 112 (i.e., ground truth or reference). In some cases, parameters such as heart model 112, ROI 136, at least a view point 140, corresponding view angle 144 may be adjusted during medical image generation, simulating various clinical scenarios or patient populations, aiding in creating machine learning models that developed for solving problems under different clinical scenarios based on patient's medical images. In some cases, image generator 156 may be able to produce a vast number of unique images, much more than what may be feasible to collect in a real-world clinical settings. Such large volume of data may be beneficial for training deep learning machine learning models, which typically require extensive datasets to achieve desired performance. Additionally, or alternatively, processor 104 may perform data augmentation techniques on generated medical images, for example, and without limitation, rotations, scaling, or even small deformations may be applied, further expanding the dataset. In a non-limiting example, a cardiac anatomy modeling model as described in U.S. patent application Ser. No. 18/376,688, configured for generating a 3D model of a heart based on ICE images pertaining to a patient may be trained using such generated training data. As a person skilled in the art, upon reviewing the entirety of this disclosure, will recognize the importance of using synthesized medical images in training machine learning models.

With continued reference to FIG. 1, it should be noted that apparatus 100 and methods described herein are not limited to cardiac applications but are expansively applicable to other organs, for instance, and without limitation, echo sensor's visualization capabilities when employed to compute the location and orientation of the sensor (i.e., ROI 136) within an organ may be effectively adapted for use within liver or other anatomical structures where precision and minimally invasive diagnostics are crucial. As a person skilled in the art, upon reviewing the entirety of this disclosure, will recognize one or more embodiments described herein (although principally focused on the heart), the underlaying principles may be readily transposable to a broader spectrum of medical imaging and intervention applications such as, without limitation, transcatheter intervention (which is rapidly supplanting traditional open surgery) that is not currently disclosed.

Figure 2:
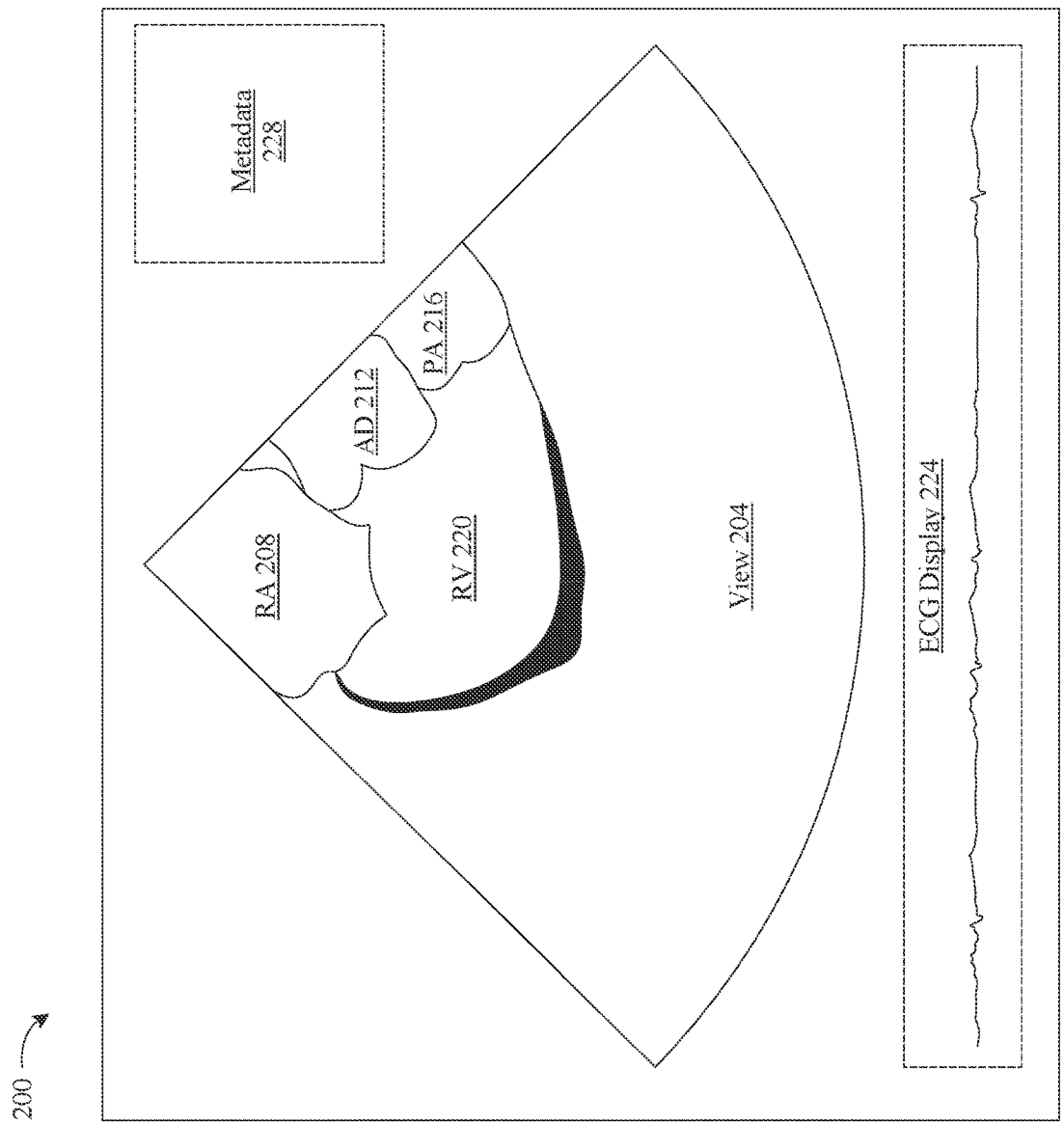
FIG. 2 shows an exemplary embodiment of a medical image.

Now referring to FIG. 2, an exemplary embodiment of a medical image 200 is illustrated. As described above with reference to FIG. 1, medical image 200 may include an ICE image. In some cases, medical image 200 may include a plurality of ICE images, wherein the plurality of ICE images may be further compiled into a (ICE) video 176 as described above. In an embodiment, ICE image 200 may be real-time, dynamic ultrasound image that provide a (detailed) view 204 of heart's interior structures, including, without limitation, right atrium (RA) 208, anterior descending (AD) 212, pulmonary atresia (PA) 216, and right ventricular (RV) 220.

With continued reference to FIG. 2, in some cases, medical image 200 may include gray scaled image. It should be noted that, in some cases, medical image 200 may be configured to visualize blood flow and/or blood flow patterns within the heart via color doppler as described above with FIG. 1. In some cases, resolution and/or clarity of medical image 200 such as ICE image as described herein may be superior to transthoracic or transesophageal echocardiography due to the ICE catheter may be positioned inside the heart, closer to the structures being imaged.

Still referring to FIG. 2, in a non-limiting example, heart chambers 208 may appear as dark, anechoic (black) areas since they are filled with blood, which doesn't reflect ultrasound waves well. Heart walls, valves, and/or other structures may appear as varying shades of gray, depending on their density and composition, in some cases, Color Doppler overlays may show blood flow in different colors, indicating the direction and speed of blood flow. For instance, and without limitation, red may indicate flow towards the probe, while blue may indicate flow away from the probe.

With continued reference to FIG. 2, in a non-limiting embodiment, medical image 200 may be synchronized with ECG data as described above with reference to FIG. 1, allowing for precise timing of cardiac events with anatomical visualization provided by medical image 200 such as ICE image. In some cases, ICE image may include a ECG display 224 configured to display ECG waveform as a continuous line graph at the top, bottom, or side of ICE image. In some cases, specific parts of the cardiac cycle e.g., systole or diastole, may be correlated with visual data from medical image 200.

Additionally, or alternatively, and still referring to FIG. 2, medical image 200 may come with accompanying metadata 228 displayed on the side or corners of medical image 200 as described herein. In some cases, metadata 228 may provide essential contextual information about medical image 200 and/or the corresponding patient. In a non-limiting example, metadata 228 may include patient information (e.g., patient ID, name, DOB, age, gender, and the like), image acquisition details (e.g., date and time, probe type, frequency, depth, gain, and the like), procedure-related information (e.g., procedure name, operator, location, and the like), ECG trace (e.g., ECG data as described above), measurement annotations (e.g., any measurements taken directly on the image e.g., diameter, a value of thickness of a heart wall and the like), image sequence information (e.g., image number, total number of frames, and the like), comments or notes, hospital or clinic information, and/or the like. As an ordinary person skilled in the art, upon reviewing the entirety of this disclosure, will be aware of medical image 200 and various components thereof may be incorporated by apparatus 100 for generating 3D model of cardiac anatomy.

Figure 3:
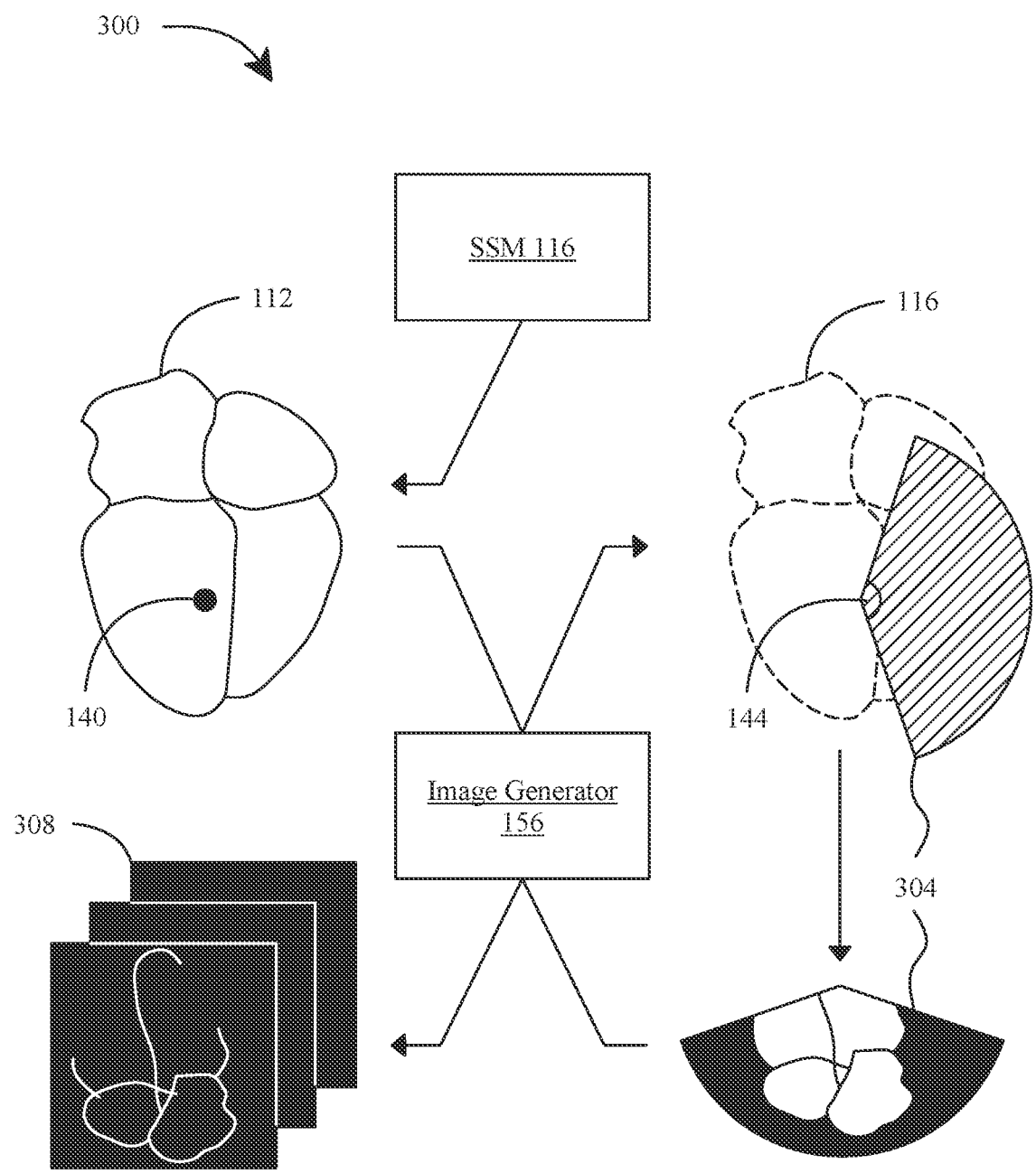
FIG. 3 is a flow diagram of an exemplary embodiment of a medical image synthesis.

Now referring to FIG. 3, a flow diagram of an exemplary embodiment of an medical image data generation process 300. In an embodiment, medical image training data as described above with reference to FIG. 1 may be generated, at least in part, through medical image generation process 300. In some cases, processor 104 may be configured to receive a heart model 112 and identify an ROI 136 based on the received heart model 112. A FOV 304, defined by at least a point of view 140 and corresponding view angle 144 may be determined to capture ROI 136. In some cases, heart model 112 received by processor 104 may be derived from CT scans using SSM 116 as described above with reference to FIG. 1. Medical image e.g., a synthetic ICE frame 308 may then be generated, by processor 104, as a function of FOV 304. As used in this disclosure, a "synthetic ICE frame" refers to a digitally generated or simulated image that emulates a visual representation obtained from ICE view 304. In some cases, synthetic ICE frames 308 may be produced using computational methods and/or models such as, without limitation, an image generator 156 having one or more camera transformation program 160 and/or generative machine learning models based on pre-existing data, models, or simulations e.g., heart model 112. In a non-limiting example, synthetic ICE frames 308 may include a simplified version e.g., an image illustrating heart anatomy via a plurality of lines indicating contours of heart's structure as shown in FIG. 3. One or more image processing techniques and/or computer vision algorithms as described above with reference to FIG. 1, such as, without limitation, histogram equalization, adaptive filtering, edge detection (e.g., Canny or Sobel operators), contour extraction, and/or the like may be applied, by imaging processing module and/or computer vision module as described above, on FOV 304. Synthetic ICE frame 308 may be rendered on a blank canvas or background that mimics the echogenicity of an ICE image according to extracted contours, wherein the extracted contours may be represented as a bold lines and enhanced with shading to give depth. In some cases, synthetic ICE frame 308 may be validated and verified by overlaying synthetic ICE frame 308 onto FOV 304, ensuring accuracy and resemblance.

Figure 4:
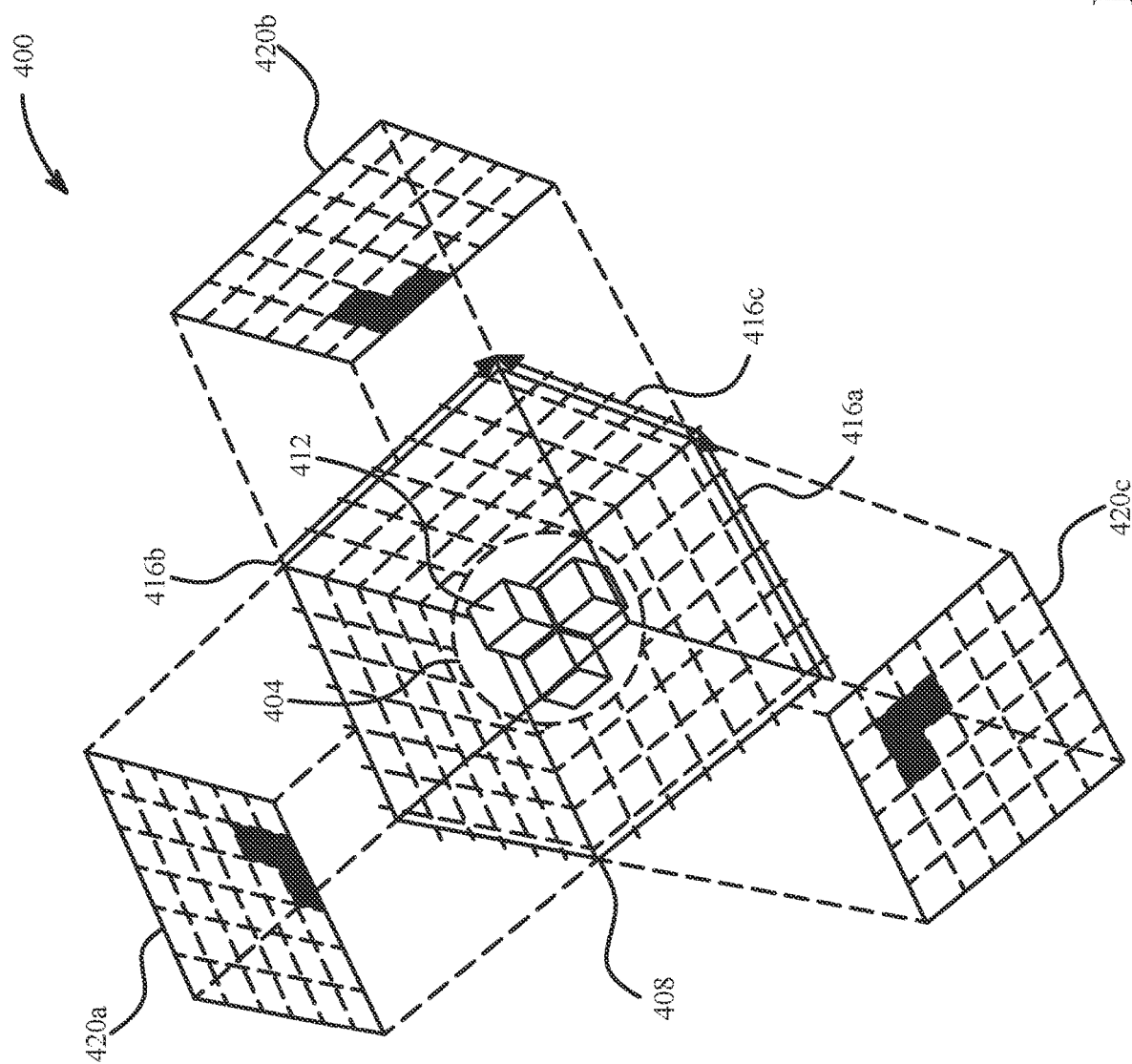
FIG. 4 illustrates an exemplary embodiment of a three-dimensional (3D) voxel occupancy representation.

Now referring to FIG. 4, an exemplary embodiment of a 3D VOR 400 is illustrated. 3D VOR 400 may be used to represent 3D object 404. In an embodiment, 3D VOR 400 may divide a 3D space 408 into a grid of one or more cubic units e.g., voxels 412, wherein each voxel 412 represents a specific volume within 3D space 408. In a non-limiting example, 3D object 404 may include a heart model 112 pertaining to patient's heart.

Still referring to FIG. 4, in some cases, each voxel 412 may act as a basic building block. In a non-limiting example, each voxel 412 may be configured to represent a discrete portion of 3D space 408. In an embodiment, each voxel 412 may include a presence indicator as described above with reference to FIG. 1, which denotes whether the voxel is occupied or unoccupied. In such embodiment, the binary or continuous value may allow 3D VOR 400 to map the presence or absence of material within each voxel 412, creating a granular representation of 3D object 404.

With continued reference to FIG. 4, in some cases, the resolution of 3D VOR 400 may be determined by the size and number of voxels within the grid. In a non-limiting example, smaller voxel may provide a higher resolution, capturing finer details, while larger voxels offer a more generalized representation.

Still referring to FIG. 4, in an embodiment, voxels 412 may be arranged in a regular pattern along three axis 416*a-b*, each pointing a distinct direction. In a non-limiting example, voxels 412 may be arranged along x, y, and z axes, wherein such arrange may facilitate efficient manipulation and rendering of the 3D object 404. In some cases, spatial model features 420*a-c* such as, without limitation, edges, surfaces, textures, and any other spatial features as described above with reference to FIG. 1, may be extracted from 3D VOR 400 by analyzing the relationships and patterns between neighboring voxels.

Figure 5:
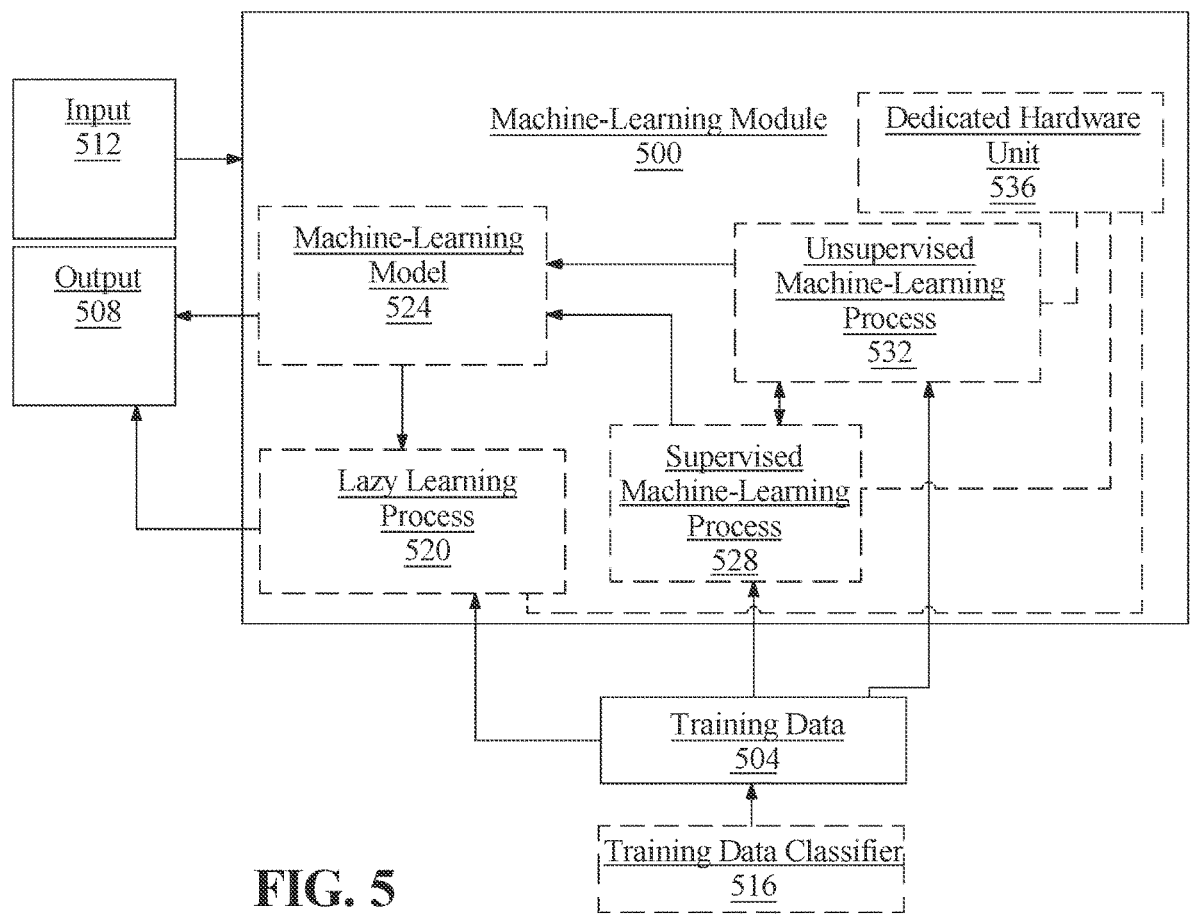
FIG. 5 is a block diagram of an exemplary machine-learning process.

Referring now to FIG. 5, an exemplary embodiment of a machine-learning module 500 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 504 to generate an algorithm instantiated in hardware or software logic, data structures, and/or functions that will be performed by a computing device/module to produce outputs 508 given data provided as inputs 512; this is in contrast to a non-machine learning software program where the commands to be executed are determined in advance by a user and written in a programming language.

Still referring to FIG. 5, "training data," as used herein, is data containing correlations that a machine-learning process may use to model relationships between two or more categories of data elements. For instance, and without limitation, training data 504 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 504 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 504 according to various correlations; correlations may indicate causative and/or predictive links between categories of data elements, which may be modeled as relationships such as mathematical relationships by machine-learning processes as described in further detail below. Training data 504 may be formatted and/or organized by categories of data elements, for instance by associating data elements with one or more descriptors corresponding to categories of data elements. As a non-limiting example, training data 504 may include data entered in standardized forms by persons or processes, such that entry of a given data element in a given field in a form may be mapped to one or more descriptors of categories. Elements in training data 504 may be linked to descriptors of categories by tags, tokens, or other data elements; for instance, and without limitation, training data 504 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 5, training data 504 may include one or more elements that are not categorized; that is, training data 504 may not be formatted or contain descriptors for some elements of data. Machine-learning algorithms and/or other processes may sort training data 504 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 504 to be made applicable for two or more distinct machine-learning algorithms as described in further detail below. Training data 504 used by machine-learning module 500 may correlate any input data as described in this disclosure to any output data as described in this disclosure. As a non-limiting illustrative example, heart models and/or patient profiles may be correlated with ROIs as training data that may be used to train ROI identification model as described above with reference to FIG. 1 to automatically identify ROI.

Further referring to FIG. 5, training data may be filtered, sorted, and/or selected using one or more supervised and/or unsupervised machine-learning processes and/or models as described in further detail below; such models may include without limitation a training data classifier 516. Training data classifier 516 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 500 may generate a classifier using a classification algorithm, defined as a processes whereby a computing device and/or any module and/or component operating thereon derives a classifier from training data 504. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers.

With further reference to FIG. 5, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Still referring to FIG. 5, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively, or additionally, one or more training examples may be identified as having poor quality data, where "poor quality" is defined as having a signal to noise ratio below a threshold value.

As a non-limiting example, and with further reference to FIG. 5, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity, and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 5, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively, or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 5, computing device, processor, and/or module may down-sample elements of a training example to a desired lower number of data elements. As a non-limiting example, a high pixel count image may have 256 pixels, however a desired number of pixels may be 128. Processor may down-sample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Still referring to FIG. 5, machine-learning module 500 may be configured to perform a lazy-learning process 520 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 504. Heuristic may include selecting some number of highest-ranking associations and/or training data 504 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 5, machine-learning processes as described in this disclosure may be used to generate machine-learning models 524. A "machine-learning model," as used in this disclosure, is a data structure representing and/or instantiating a mathematical and/or algorithmic representation of a relationship between inputs and outputs, as generated using any machine-learning process including without limitation any process as described above and stored in memory; an input is submitted to a machine-learning model 524 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 524 may be generated by creating an artificial neural network, such as a convolutional neural network comprising an input layer of nodes, one or more intermediate layers, and an output layer of nodes. Connections between nodes may be created via the process of "training" the network, in which elements from a training data 504 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 5, machine-learning algorithms may include at least a supervised machine-learning process 528. At least a supervised machine-learning process 528, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include a plurality heart models and patient profile as described above as inputs, a plurality of ROIs as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 504. Persons skilled in the art, upon reviewing the entirety of this disclosure, will be aware of various possible variations of at least a supervised machine-learning process 528 that may be used to determine relation between inputs and outputs. Supervised machine-learning processes may include classification algorithms as defined above.

With further reference to FIG. 5, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 5, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 5, machine learning processes may include at least an unsupervised machine-learning processes 532. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 532 may not require a response variable; unsupervised processes 532 may be used to find interesting patterns and/or inferences between variables, to determine a degree of correlation between two or more variables, or the like.

Still referring to FIG. 5, machine-learning module 500 may be designed and configured to create a machine-learning model 524 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 5, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 5, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 5, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 5, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 5, one or more processes or algorithms described above may be performed by at least a dedicated hardware unit 536. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 536 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 536 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 536 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 6:
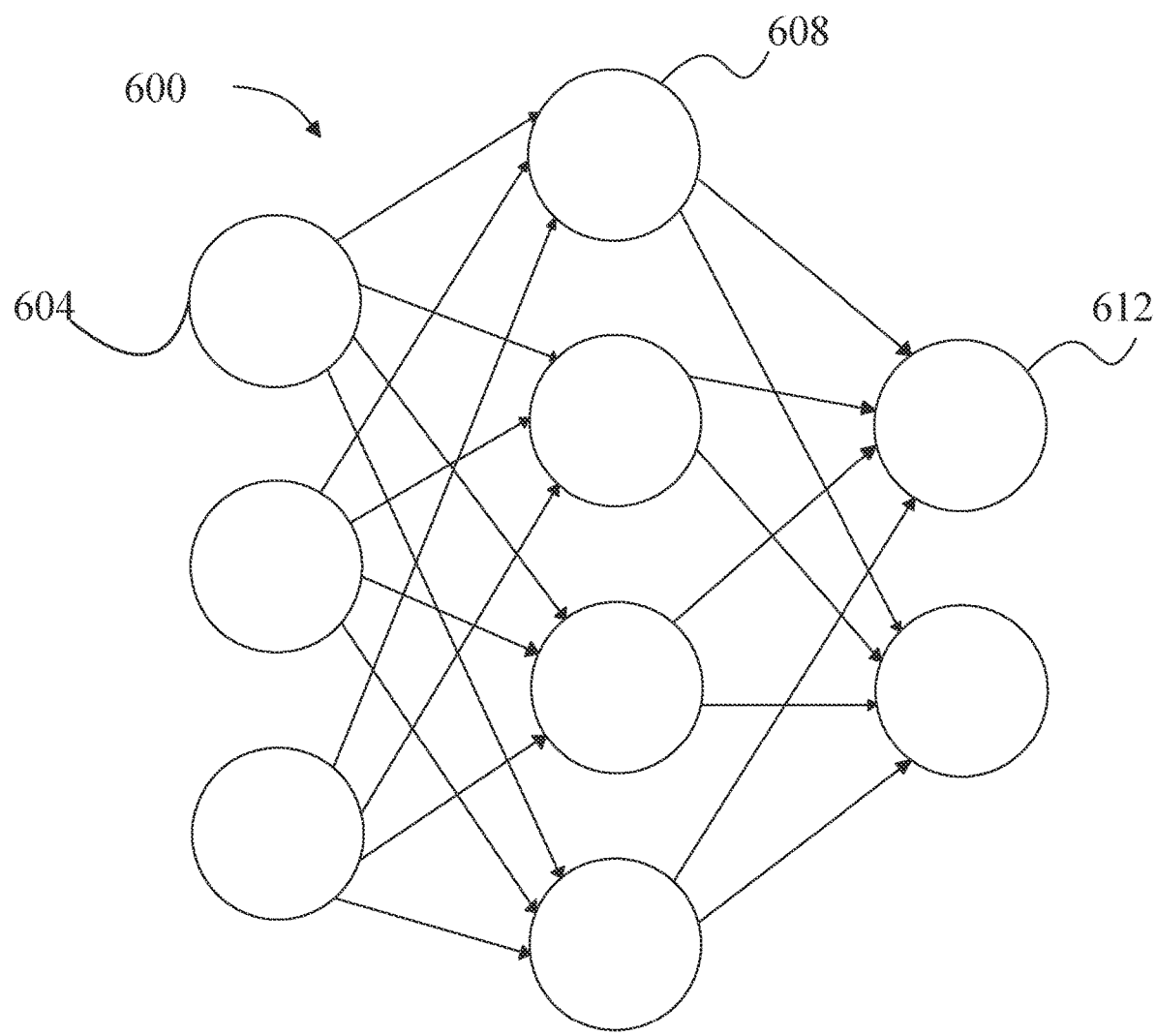
FIG. 6 is a diagram of an exemplary embodiment of a neural network.

Referring now to FIG. 6, an exemplary embodiment of neural network 600 is illustrated. A neural network 600 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 604, one or more intermediate layers 608, and an output layer of nodes 612. Connections between nodes may be created via the process of "training" the network, in which elements from a training data set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network or may feed outputs of one layer back to inputs of the same or a different layer in a "recurrent network." As a further non-limiting example, a neural network may include a convolutional neural network comprising an input layer of nodes, one or more intermediate layers, and an output layer of nodes.

With continued reference to FIG. 6, in an embodiment, neural network 600 may include a deep neural network (DNN). As used in this disclosure, a "deep neural network" is defined as a neural network with two or more hidden layers. In a non-limiting example, deep neural network may include a convolutional neural network (CNN). Identifying ROI may include training CNN using plurality of heart models as input correlated to a plurality of ROI as output and identify ROI using trained CNN. A "convolutional neural network," for the purpose of this disclosure, is a neural network in which at least one hidden layer is a convolutional layer that convolves inputs to that layer with a subset of inputs known as a "kernel," along with one or more additional layers such as pooling layers, fully connected layers, and the like. In some cases, CNN may include, without limitation, a deep neural network (DNN) extension. Mathematical (or convolution) operations performed in the convolutional layer may include convolution of two or more functions, where the kernel may be applied to input data e.g., heart model 112 through a sliding window approach. In some cases, convolution operations may enable processor 104 to detect local/global patterns, edges, textures, and any other features described herein within heart model 112. Spatial features 140 may be passed through one or more activation functions, such as without limitation, Rectified Linear Unit (ReLU), to introduce non-linearities into the processing step of identifying ROI. Additionally, or alternatively, CNN may also include one or more pooling layers, wherein each pooling layer is configured to reduce the dimensionality of input data while preserving essential features within the input data. In a non-limiting example, CNN may include one or more pooling layer configured to reduce the spatial dimensions of spatial feature maps by applying downsampling, such as max-pooling or average pooling, to small, non-overlapping regions of one or more features.

Still referring to FIG. 1, CNN may further include one or more fully connected layers configured to combine features extracted by the convolutional and pooling layers as described above. In some cases, one or more fully connected layers may allow for higher-level pattern recognition. In a non-limiting example, one or more fully connected layers may connect every neuron (i.e., node) in its input to every neuron in its output, functioning as a traditional feedforward neural network layer. In some cases, one or more fully connected layers may be used at the end of CNN to perform high-level reasoning and produce the final output such as, without limitation, desired ROIs. Further, each fully connected layer may be followed by one or more dropout layers configured to prevent overfitting, and one or more normalization layers to stabilize the learning process described herein.

With continued reference to FIG. 6, CNN may further include a 3D CNN, wherein the 3D CNN, unlike standard 2D CNN, may include utilization of one or more 3D convolutions which allow them to directly process 3D data. In a non-limiting example, 3D CNN may include one or more 3D filters (i.e., kernels) that move through heart model 112 in three dimensions and capturing spatial relationships in x, y, and z axis. Similar to 3D convolutions, 3D CNN may further include one or more 3D pooling layers that may be used to reduce the dimensionality of heart model 112 while preserving spatial features as described above. Additionally, or alternatively, an encoder-decoder structure may be implemented (extended to 3D), by processor 104, in 3D CNN, wherein the encoder-decoder structure includes an encoding path that captures the context and a decoding path that enables precise localization in a same manner as U-net as described above. Such encoder-decoder structures may also include a plurality of skip connections, allowing 3D CNN to use information from multiple resolutions to improve the process of ROI identification.

With continued reference to FIG. 6, in an embodiment, training the CNN may include selecting a suitable loss function to guide the training process. In a non-limiting example, a loss function that measures the difference between the predicted output and the ground truth may be used, such as, without limitation, mean squared error (MSE) or a custom loss function may be designed for one or more embodiments described herein. Additionally, or alternatively, optimization algorithms, such as stochastic gradient descent (SGD), may then be used to adjust the neural network's parameters to minimize such loss. In a further non-limiting embodiment, instead of directly identifying ROI, CNN may be trained as a regression model to predict a coordinate of at least a view point and corresponding view angle in a numeric format. Additionally, CNN may be extended with additional deep learning techniques, such as recurrent neural networks (RNNs) or attention mechanism, to capture additional features and/or data relationships within input data.

Figure 7:
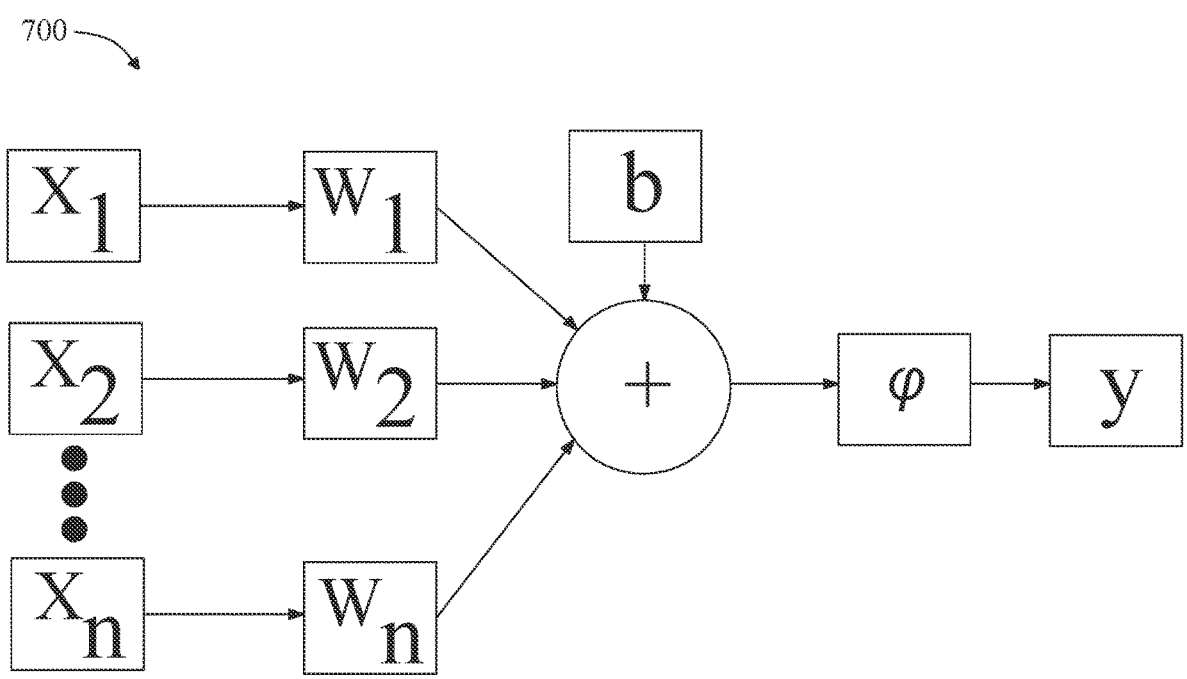
FIG. 7 is a diagram of an exemplary embodiment of a node of a neural network.

Referring now to FIG. 7, an exemplary embodiment of a node 700 of a neural network is illustrated. A node may include, without limitation, a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1 - e^{-x}}$$

given input x, a tanh (hyperbolic tangent) function, of the form $$\frac{e^x - e^{-x}}{e^x + e^{-x}},$$

a tanh derivative function such as f (x)=tanh$^2$(x), a rectified linear unit function such as f(x)=max (0, x), a "leaky" and/or "parametric" rectified linear unit function such as f(x)=max (ax, x) for some a, an exponential linear units function such as $$f(x) = \begin{cases} x \text{ for } x \geq 0 \\ \alpha(e^x - 1) \text{ for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as f(x)=x*sigmoid (x), a Gaussian error linear unit function such as f(x)=a (1+tanh ($\sqrt{2/\pi}$(x+bx$^r$))) for some values of a, b, and r, and/or a scaled exponential linear unit function such as $$f(x) = \lambda \begin{cases} \alpha(e^x - 1) \text{ for } x < 0 \\ x \text{ for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally, or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input x/may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 8:
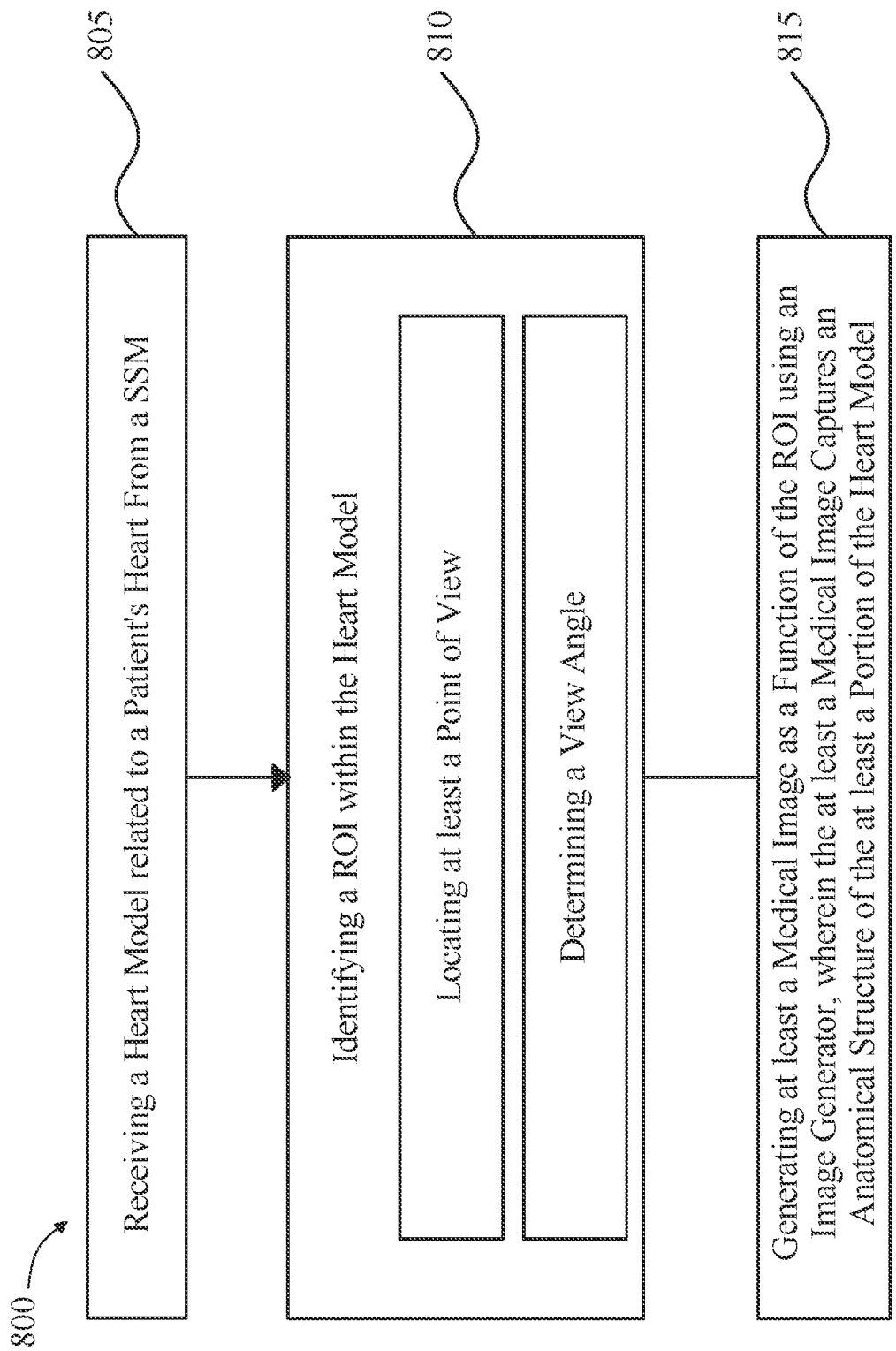
FIG. 8 is a flow diagram illustrating an exemplary embodiment of a method for generating a three-dimensional (3D) model of cardiac anatomy via machine-learning.

Now referring to FIG. 8, a flow diagram of an exemplary method 800 for synthetizing medical images is illustrated. The method 800 includes a step 805 of receiving, by at least a processor, a heart model related to a patient's heart. In some embodiments, receiving the heart model may include constructing the heart model based on a patient profile pertaining to the patient using a computer vision module, wherein the patient profile may include a plurality of computed tomography (CT) scans of the patient's heart and associated metadata. In some cases, the patient profile further may include electrocardiogram (ECG) data. In some embodiments, receiving the heart model may include transforming the heart model to a second heart model using a statistical shape model as a function of a plurality of mode changers within the Statistical Shape Model, wherein each mode changer of the plurality of mode changers is associated with a model feature of the heart model. In other cases, the heart model may include a 3D voxel occupancy representation (VOR) of the patient's heart. This may be implemented, without limitation, as described above with reference to FIGS. 1-7.

With continued reference to FIG. 8, method 800 includes a step 810 of identifying, by the at least a processor, a region of interest within the heart model, wherein identifying the region of interest includes locating at least a point of view on the heart model and determining a view angle corresponding to the at least a point of view, wherein the at least a point of view and the corresponding view angle define at least one field of view that include at least a portion of the heart model. This may be implemented, without limitation, as described above with reference to FIGS. 1-7.

With continued reference to FIG. 8, method 800 includes a step 815 of generating, by the at least a processor, at least a medical image as a function of the region of interest using an image generator, wherein the at least a medical image captures an anatomical structure of the at least a portion of the heart model. In some embodiments, generating the at least a medical image may include executing a camera transformation program configured to simulate at least a perspective of an ICE probe or other probe using the image generator. In some cases, executing the camera transformation program may include generating a projection of the anatomical structure by rendering the ROI as a function of a set of imaging parameters using a virtual camera positioned at the at least a point of view with the corresponding view angle. In some cases, the image generator may include a generative adversarial network (GAN). In some embodiments, generating the at least a medical image may include training the GAN using a plurality of anatomical structure projections and synthesizing at least a medical image using the trained GAN at the at least a point of view with the corresponding view angle. This may be implemented, without limitation, as described above with reference to FIGS. 1-7.

With continued reference to FIG. 8, method 800 may further include a step of compiling, by the at least a processor, a plurality of medical images into a video as a function of the ECG data, wherein the video is synchronized with a cardiac cycle indicated by the ECG data. This may be implemented, without limitation, as described above with reference to FIGS. 1-7.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 9:
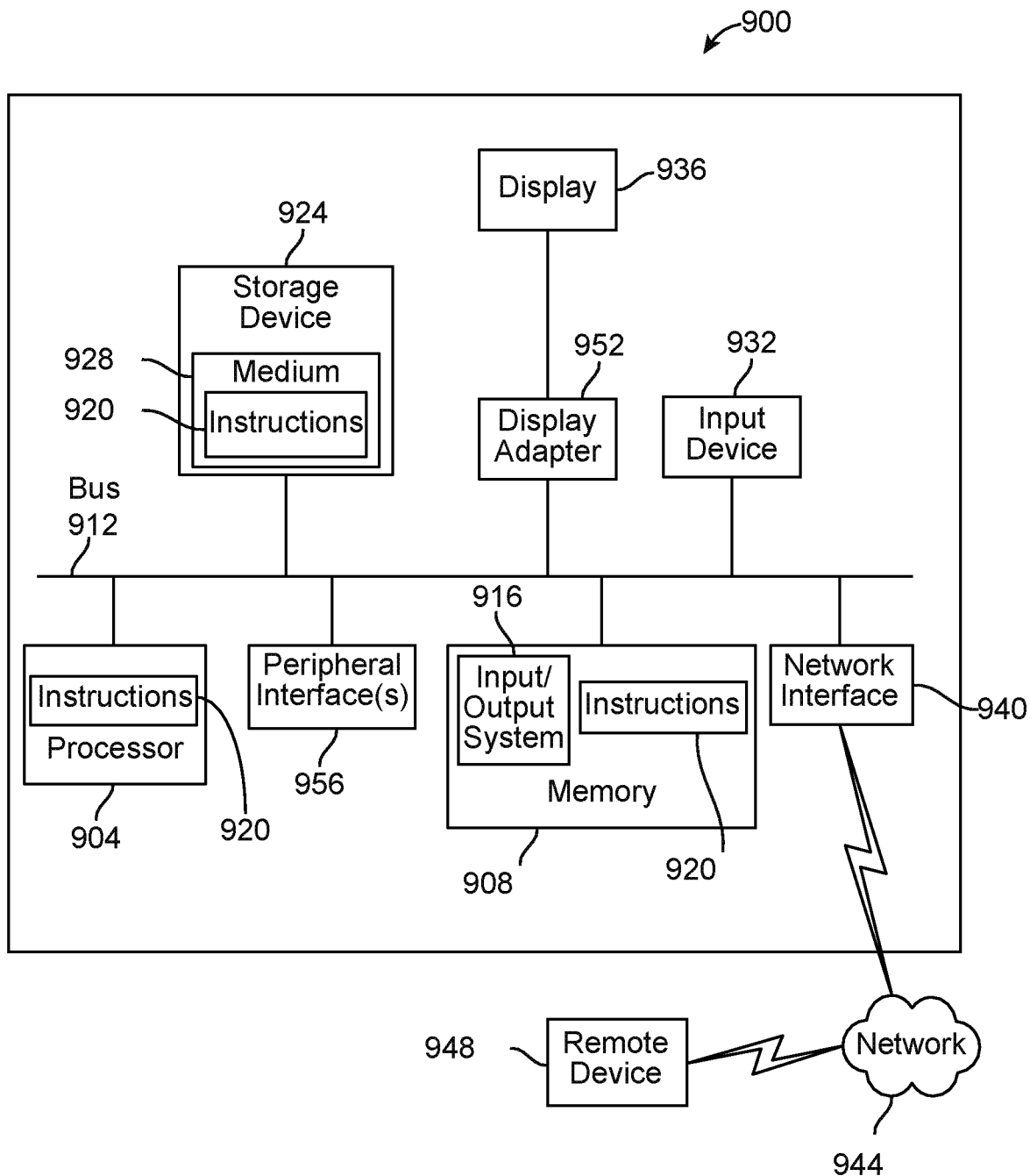
FIG. 9 is a block diagram of a computing system that can be used to implement any one or more of the methodologies disclosed herein and any one or more portions thereof.

FIG. 9 shows a diagrammatic representation of one embodiment of a computing device in the exemplary form of a computer system 900 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 900 includes a processor 904 and a memory 908 that communicate with each other, and with other components, via a bus 912. Bus 912 may include any of several types of bus structures including, but not limited to, a memory bus, a memory controller, a peripheral bus, a local bus, and any combinations thereof, using any of a variety of bus architectures.

Processor 904 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 904 may be organized according to Von Neumann and/or Harvard architecture as a non-limiting example. Processor 904 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 908 may include various components (e.g., machine-readable media) including, but not limited to, a random-access memory component, a read only component, and any combinations thereof. In one example, a basic input/output system 916 (BIOS), including basic routines that help to transfer information between elements within computer system 900, such as during start-up, may be stored in memory 908. Memory 908 may also include (e.g., stored on one or more machine-readable media) instructions (e.g., software) 920 embodying any one or more of the aspects and/or methodologies of the present disclosure. In another example, memory 908 may further include any number of program modules including, but not limited to, an operating system, one or more application programs, other program modules, program data, and any combinations thereof.

Computer system 900 may also include a storage device 924. Examples of a storage device (e.g., storage device 924) include, but are not limited to, a hard disk drive, a magnetic disk drive, an optical disc drive in combination with an optical medium, a solid-state memory device, and any combinations thereof. Storage device 924 may be connected to bus 912 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 924 (or one or more components thereof) may be removably interfaced with computer system 900 (e.g., via an external port connector (not shown)). Particularly, storage device 924 and an associated machine-readable medium 928 may provide nonvolatile and/or volatile storage of machine-readable instructions, data structures, program modules, and/or other data for computer system 900. In one example, software 920 may reside, completely or partially, within machine-readable medium 928. In another example, software 920 may reside, completely or partially, within processor 904.

Computer system 900 may also include an input device 932. In one example, a user of computer system 900 may enter commands and/or other information into computer system 900 via input device 932. Examples of an input device 932 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 932 may be interfaced to bus 912 via any of a variety of interfaces (not shown) including, but not limited to, a serial interface, a parallel interface, a game port, a USB interface, a FIREWIRE interface, a direct interface to bus 912, and any combinations thereof. Input device 932 may include a touch screen interface that may be a part of or separate from display 936, discussed further below. Input device 932 may be utilized as a user selection device for selecting one or more graphical representations in a graphical interface as described above.

A user may also input commands and/or other information to computer system 900 via storage device 924 (e.g., a removable disk drive, a flash drive, etc.) and/or network interface device 940. A network interface device, such as network interface device 940, may be utilized for connecting computer system 900 to one or more of a variety of networks, such as network 944, and one or more remote devices 948 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 944, may employ a wired and/or a wireless mode of communication. In general, any network topology may be used. Information (e.g., data, software 920, etc.) may be communicated to and/or from computer system 900 via network interface device 940.

Computer system 900 may further include a video display adapter 952 for communicating a displayable image to a display device, such as display device 936. Examples of a display device include, but are not limited to, a liquid crystal display (LCD), a cathode ray tube (CRT), a plasma display, a light emitting diode (LED) display, and any combinations thereof. Display adapter 952 and display device 936 may be utilized in combination with processor 904 to provide graphical representations of aspects of the present disclosure. In addition to a display device, computer system 900 may include one or more other peripheral output devices including, but not limited to, an audio speaker, a printer, and any combinations thereof. Such peripheral output devices may be connected to bus 912 via a peripheral interface 956. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. An apparatus for synthetizing medical images, wherein the apparatus comprises:
   at least a processor; and
   a memory communicatively connected to the at least a processor, wherein the memory contains instructions configuring the at least a processor to:
   receive a heart model related to a patient's heart;
   identify a region of interest within the heart model, wherein identifying the region of interest comprises:
   locating at least a point of view on the heart model; and
   determining a view angle corresponding to the at least a point of view, wherein the at least a point of view and the corresponding view angle define at least one field of view that includes at least a portion of the heart model; and
   generate at least a medical image as a function of the region of interest using an image generator, wherein the at least a medical image captures an anatomical structure of the at least a portion of the heart model, wherein the medical image comprises a real-time visualization of cardiac anatomy, wherein the image generator comprises a generative model comprising at least a variational autoencoder configured to allow data sample generation to be applied in a training of the image generator.

2. The apparatus of claim 1, wherein receiving the heart model comprises:
   constructing the heart model based on a patient profile pertaining to the patient using a computer vision module, wherein the patient profile comprises a set of images of the patient's heart and associated metadata.

3. The apparatus of claim 2, wherein the patient profile further comprises electrocardiogram (ECG) data.

4. The apparatus of claim 1, wherein receiving the heart model further comprises:
   transforming the heart model to a second heart model using a Statistical Shape Model as a function of a plurality of mode changers within the Statistical Shape Model, wherein each mode changer of the plurality of mode changers is associated with a model feature of the heart model.

5. The apparatus of claim 1, wherein the heart model comprises a 3D voxel occupancy representation (VOR) of the patient's heart.

6. The apparatus of claim 1, wherein generating the at least a medical image further comprises:
   executing a camera transformation program configured to simulate at least a perspective of a probe using the image generator.

7. The apparatus of claim 6, wherein executing the camera transformation program comprises:
   generating a projection of the anatomical structure by rendering the region of interest (ROI) as a function of a set of imaging parameters using a virtual camera positioned at the at least a point of view with the corresponding view angle.

8. The apparatus of claim 1, wherein the image generator comprises a generative adversarial network (GAN).

9. The apparatus of claim 8, wherein generating the at least a medical image further comprises:
   training the GAN using a plurality of anatomical structure projections; and
   synthesizing the at least a medical image using the trained GAN at the at least a point of view with the corresponding view angle.

10. The apparatus of claim 3, wherein the memory contains instructions further configuring the at least a processor to:
    compile a plurality of medical images into a video as a function of the ECG data, wherein the video is synchronized with a cardiac cycle indicated by the ECG data.

11. A method for synthetizing medical images, wherein the method comprises:
    receiving, by at least a processor, a heart model related to a patient's heart;
    identifying, by the at least a processor, a region of interest which changes over time, within the heart model, wherein identifying the region of interest comprises:
    locating at least a point of view on the heart model; and
    determining a view angle corresponding to the at least a point of view, wherein the at least a point of view and the corresponding view angle define at least one field of view that includes at least a portion of the heart model; and
    generating, by the at least a processor, at least a medical image as a function of the region of interest using an image generator, wherein the at least a medical image captures an anatomical structure of the at least a portion of the heart model, wherein the medical image comprises a real-time visualization of cardiac anatomy, wherein the image generator comprises a generative model comprising at least a variational autoencoder configured to allow data sample generation to be applied in a training of the image generator.

12. The method of claim 11, wherein receiving the heart model further comprises:
constructing the heart model based on a patient profile pertaining to the patient using a computer vision module, wherein the patient profile comprises a set of images of the patient's heart and associated metadata.

13. The method of claim 12, wherein the patient profile further comprises electrocardiogram (ECG) data.

14. The method of claim 11, wherein receiving the heart model further comprises:
transforming the heart model to a second heart model using a Statistical Shape Model as a function of a plurality of mode changers within the Statistical Shape Model, wherein each mode changer of the plurality of mode changers is associated with a model feature of the heart model.

15. The method of claim 11, wherein the heart model comprises a 3D voxel occupancy representation (VOR) of the patient's heart.

16. The method of claim 11, wherein generating the at least a medical image further comprises:
executing a camera transformation program configured to simulate at least a perspective of a probe using the image generator.

17. The method of claim 16, wherein executing the camera transformation program comprises:
generating a projection of the anatomical structure by rendering the region of interest (ROI) as a function of a set of imaging parameters using a virtual camera positioned at the at least a point of view with the corresponding view angle.

18. The method of claim 11, wherein the image generator comprises a generative adversarial network (GAN).

19. The method of claim 18, wherein generating the at least a medical image further comprises:
training the GAN using a plurality of anatomical structure projections; and
synthesizing at least a medical image using the trained GAN at the at least a point of view with the corresponding view angle.

20. The method of claim 13, further comprising:
compiling, by the at least a processor, a plurality of medical images into a video as a function of the ECG data, wherein the video is synchronized with a cardiac cycle indicated by the ECG data.

* * * * *